US010975355B2

(12) United States Patent
Hebrok et al.

(10) Patent No.: US 10,975,355 B2
(45) Date of Patent: Apr. 13, 2021

(54) CONTROLLED INDUCTION OF HUMAN PANCREATIC PROGENITORS PRODUCES FUNCTIONAL BETA-LIKE CELLS

(71) Applicant: THE REGENTS OF THE UNIVERSITY OF CALIFORNIA, Oakland, CA (US)

(72) Inventors: Matthias Hebrok, Belmont, CA (US); Holger Andreas Russ, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/568,736

(22) PCT Filed: Apr. 22, 2016

(86) PCT No.: PCT/US2016/028963
§ 371 (c)(1),
(2) Date: Oct. 23, 2017

(87) PCT Pub. No.: WO2016/172564
PCT Pub. Date: Oct. 27, 2016

(65) Prior Publication Data
US 2018/0087034 A1    Mar. 29, 2018

Related U.S. Application Data

(60) Provisional application No. 62/151,832, filed on Apr. 23, 2015.

(51) Int. Cl.
| | |
|---|---|
| *C12N 5/071* | (2010.01) |
| *C07K 14/62* | (2006.01) |
| *C07K 14/50* | (2006.01) |
| *C07K 14/485* | (2006.01) |
| *C07K 14/495* | (2006.01) |
| *A61P 3/10* | (2006.01) |
| *A61K 35/39* | (2015.01) |

(52) U.S. Cl.
CPC ............ *C12N 5/0678* (2013.01); *A61K 35/39* (2013.01); *A61P 3/10* (2018.01); *C07K 14/485* (2013.01); *C07K 14/495* (2013.01); *C07K 14/50* (2013.01); *C07K 14/62* (2013.01); *C12N 5/0677* (2013.01); *C12N 2501/11* (2013.01); *C12N 2501/117* (2013.01); *C12N 2501/15* (2013.01); *C12N 2501/155* (2013.01); *C12N 2501/385* (2013.01); *C12N 2501/41* (2013.01); *C12N 2506/02* (2013.01)

(58) Field of Classification Search
CPC ............... C12N 5/0678; C12N 5/0677; C12N 2501/11; C12N 2501/117; C12N 2501/15; C12N 2501/155; C12N 2501/385; C12N 2501/41; C12N 2506/02; A61P 3/10; A61K 35/39; C07K 14/485; C07K 14/495; C07K 14/50; C07K 14/62
USPC ......................................................... 424/93.7
See application file for complete search history.

(56) References Cited

U.S. PATENT DOCUMENTS

| | | |
|---|---|---|
| 2010/0112691 A1 | 5/2010 | Green et al. |
| 2013/0164787 A1 | 6/2013 | Agulnick et al. |

FOREIGN PATENT DOCUMENTS

| | | | |
|---|---|---|---|
| WO | WO 2015/002724 | * | 1/2015 |
| WO | WO-2015/002724 A2 | | 1/2015 |

OTHER PUBLICATIONS

Chmielowiec et al., In Vitro Differentiation and Expansion of Human Pluripotent Stem Cell-Derived Pancreatic Progenitors, Stem Cells and Pancreas Regeneration, Special Edition, vol. 11, No. 1, (May 2014), pp. 19-34.*
Johannesson et al., FGF4and Retinoic Acid Direct Differentiation of hESCs into PDX1-Expressing Foregut Endoderm in a Time- and Concentration-Dependent Manner, PLoS ONE, vol. 4, Iss. 3, (Mar. 2009), p. 1-13.*
Schulz et al., A Scalable System for Production of Functional Pancreatic Progenitors from Human Embryonic Stem Cells, PLoS ONE, vol. 7, Iss. 5, (May 2012), p. 1-17.*
Kumar et al., Recent Developments in β-Cell Differentiation of Pluripotent Stem Cells Induced by Small and Large Molecules, International Journal of Molecular Sciences, vol. 15, No. 12, (2014), pp. 23418-23447.*
Cai et al., Generation of Homogeneous PDX1+ Pancreatic Progenitors from Human ES Cell-derived Endoderm Cells, Journal of Molecular Cell Biology, vol. 2, (2010) pp. 50-60.*
Kumar et al., "Recent Developments in β-Cell Differentiation of Pluripotent Stem Cells Induced by Small and Large Molecules," Int. J. Mol. Sci. 15:23418-23447 (2014).
Search Report from European Application No. 16783989.3 dated Oct. 25, 2018.
Barton et al., "Improvement in outcomes of clinical islet transplantation: 1999-2010," Diabetes Care 35: 1436-1445 (2012).
Bouwens et al., "The use of stem cells for pancreatic regeneration in diabetes mellitus," Nat Rev Endocrinol 9: 598-606 (2013).

(Continued)

*Primary Examiner* — Jennifer M. H. Tichy
(74) *Attorney, Agent, or Firm* — Marshall, Gerstein & Borun LLP

(57) ABSTRACT

Methods are provided for the simple, fast, effective and safe directed differentiation of embryonic stem cells into pancreatic beta-like cells secreting insulin in response to glucose levels. The cells are useful transplant therapeutics for diabetic individuals.

15 Claims, 18 Drawing Sheets

(56) References Cited

OTHER PUBLICATIONS

Cabrera et al., "The unique cytoarchitecture of human pancreatic islets has implications for islet cell function," Proc. Natl. Acad. Sci. 103(7):2334-2339 (2006).
Chen et al., "A small molecule that directs differentiation of human ESCs into the pancreatic lineage," Nat. Chem. Biol. 5:258-265 (2009).
Chmielowiec et al., "In Vitro Differentiation and Expansion of Human Pluripotent Stem Cell-Derived Pancreatic Progenitors," The Review of Diabetic Studies, 11(1):19-34 (2014).
D'Amour et al., "Efficient differentiation of human embryonic stem cells to definitive endoderm," Nat. Biotechnol. 23: 1534-1541 (2005).
D'Amour et al., "Production of pancreatic hormone-expressing endocrine cells from human embryonic stem cells," Nat. Biotechnol. 24:1392-1401 (2006).
De Krijger et al., "The midgestational human fetal pancreas contains cells coexpressing islet hormones," Developmental Biology 153: 368-375 (1992).
Efrat et al., "Making β cells from adult tissues," Trends in Endocrinology & Metabolism 23: 278-285 (2012).
Fiaschi-Taesch et al., "Induction of Human β-Cell Proliferation and Engraftment Using a Single G1/S Regulatory Molecule, cdk6," Diabetes 59:1926-1936 (2010).
Gu et al., "Direct evidence for the pancreatic lineage: NGN3+ cells are islet progenitors and are distinct from duct progenitors," Development 129:2447-2457 (2002).
Guo et al., "Factors Expressed by Murine Embryonic Pancreatic Mesenchyme Enhance Generation of Insulin-Producing Cells From hESCs," Diabetes 62:1581-1592 (2013).
Guo et al., "Inactivation of specific β cell transcription factors in type 2 diabetes," J. Clin. Invest. 123(8):3305-3316 (2013).
Haataja et al., "Proinsulin intermolecular interactions during secretory trafficking in pancreatic β cells," Journal of Biological Chemistry 288(3):1896-1906 (2013).
Hebrok, "Generating β cells from stem cells—the story so far," Cold Spring Harb Perspect Med 2:a007674, 12 pages (2012).
Hebrok, "Hedgehog signaling in pancreas development," Mech. Dev. 120:45-57 (2003).
Herrera et al., "Pancreatic cell lineage analyses in mice," Endocrine 19(3):267-278 (2002).
Hua et al., "iPSC-derived β cells model diabetes due to glucokinase deficiency," J. Clin. Invest. 127(3);1115 (2013).
International Search Report and Written Opinion from International Application No. PCT/US16/28963 dated Jul. 29, 2016.
Jennings et al., "Development of the human pancreas from foregut to endocrine commitment," Diabetes 62:3514-3522 (2013).
Johansson et al., "Temporal control of neurogenin3 activity in pancreas progenitors reveals competence windows for the generation of different endocrine cell types," Developmental Cell 12:457-465 (2007).
Kelly et al., "Cell-surface markers for the isolation of pancreatic cell types derived from human embryonic stem cells," Nat. Biotechnol. 29:750-756 (2011).
Kroon et al., "Pancreatic endoderm derived from human embryonic stem cells generates glucose-responsive insulin-secreting cells in vivo," Nat. Biotechnol. 26(4):443-452 (2008).
Liu et al., "Systematically labeling developmental stage-specific genes for the study of pancreatic β-cell differentiation from human embryonic stem cells," Cell Res. 24:1181-1200 (2014).
Maehr et al., "Generation of pluripotent stem cells from patients with type 1 diabetes," Proc. Natl. Acad. Sci. U.S.A. 106(37):15768-15773 (2009).
Mfopou et al., "Noggin, retinoids, and fibroblast growth factor regulate hepatic or pancreatic fate of human embryonic stem cells," Gastroenterology 138:2233-2245 (2010).
Micallef et I., "INS(GFP/w) human embryonic stem cells facilitate isolation of in vitro derived insulin-producing cells," Diabetologia 55:694-706 (2012).
Murtaugh et al., "Genes, signals, and lineages in pancreas development," Annu. Rev. Cell Dev. Biol. 19: 71-89 (2003).
Nostro et al., "Generation of beta cells from human pluripotent stem cells: Potential for regenerative medicine," Seminars in Cell and Developmental Biology 23(6):701-710 (2012).
Nostro et al., "Stage-specific signaling through TGFβ family members and WNT regulates patterning and pancreatic specification of human pluripotent stem cells," Development 138:861-871 (2011).
Pagliuca et al., "Generation of Functional Human Pancreatic b Cells In Vitro," Cell 159:428-439 (2014).
Pagliuca et al., "How to make a functional β-cell," Development 140:2472-2483 (2013).
Pan et al., "Pancreas organogenesis: from bud to plexus to gland," Dev. Dyn. 240:530-565 (2011).
Posselt et al., "Islet Transplantation in Type 1 Diabetic Patients Using Calcineurin Inhibitor-Free Immunosuppressive Protocols Based on T-Cell Adhesion or Costimulation Blockade," Transplantation 90(12):1595-1601 (2010).
Rezania et al., "Maturation of Human Embryonic Stem Cell-Derived Pancreatic Progenitors Into Functional Islets Capable of Treating Pre-exisitng Diabetes in Mice," Diabetes 61:2016-2029 (2012).
Rezania et al., "Production of functional glucagon-secreting a-cells from human embryonic stem cells," Diabetes 60:239-247 (2011).
Rezania et al., "Reversal of diabetes with insulin-producing cells derived in vitro from human pluripotent stem cells," Nat. Biotechnol 32(11):1121-1134 (2014).
Riedel et al., "Immunohistochemical characterisation of cells co-producing insulin and glucagon in the developing human pancreas," Diabetologia 55:372-381 (2011).
Roark et al., "Complex regulation controls Neurogenin3 proteolysis," Biol Open 1:1264-1272 (2012).
Russ et al., "Controlled induction of human pancreatic progenitors produces functional beta-like cells in vitro," The EMBO Journal 34(13)1759-1772 (2015).
Russ et al., "In-Vivo Functional Assessment of Engineered Human Insulin-Producing Cells (Artech House)" (2011).
Schaffer et al., "Ptf1a and Nkx6 Transcription Factors Function as Antagonistic Lineage Determinants in Multipotent Pancreatic Progenitors," Developmental Cell 18(6):1022-1029 (2010).
Schulz et al., "A scalable system for production of functional pancreatic progenitors from human embryonic stem cells," PLoS ONE 7(5):e37004, 17 pages (2012).
Seymour et al., "Historical Perspective: Beginnings of the -Cell: Current Perspectives in -Cell Development," Diabetes 60:364-376 (2011).
Shang et al., "β-cell dysfunction due to increased ER stress in a stem cell model of Wolfram syndrome," Diabetes 63:923-933 (2014).
Shapiro et al., "Islet transplantation in seven patients with type 1 diabetes mellitus using a glucocorticoid-free immunosuppressive regimen," N. Engl. J. Med. 343(4):230-238 (2000).
Shih et al., "A Notch-dependent molecular circuitry initiates pancreatic endocrine and ductal cell differentiation," Development 139: 2488-2499 (2012).
Shim et al., "Pancreatic islet-like three dimensional aggregates derived from human embryonic stem cells ameliorate hyperglycemia in streptozotocin induced diabetic mice," Cell transplant. 24:2155-2168 (2015).
Szot et al., "Tolerance Induction and Reversal of Diabetes in Mice Transplanted with Human Embryonic-Stem-Cell-Derived Pancreatic Endoderm," Cell Stem Cell 16:148-157 (2015).
Szot et al., "Transplantation of Pancreatic Islets Into the Kidney Capsule of Diabetic Mice," J Vis Exp. (2007).
Tudurí et al., "Reprogramming gut and pancreas endocrine cells to treat diabetes," Diabetes, Obesity and Metabolism 13(Suppl 1):53-59 (2011).
Van Hoof et al., "Differentiation of human embryonic stem cells into pancreatic endoderm in patterned size-controlled clusters," Stem Cell Res 6:276-285 (2011).
Xu et al., "Activin, BMP and FGF pathways cooperate to promote endoderm and pancreatic lineage cell differentiation from human embryonic stem cells," Mech. Dev 128:412-427 (2011).

(56) References Cited

OTHER PUBLICATIONS

Zhou et al., "Extreme makeover: converting one cell into another," Cell Stem Cell 3:382-388 (2008).

* cited by examiner

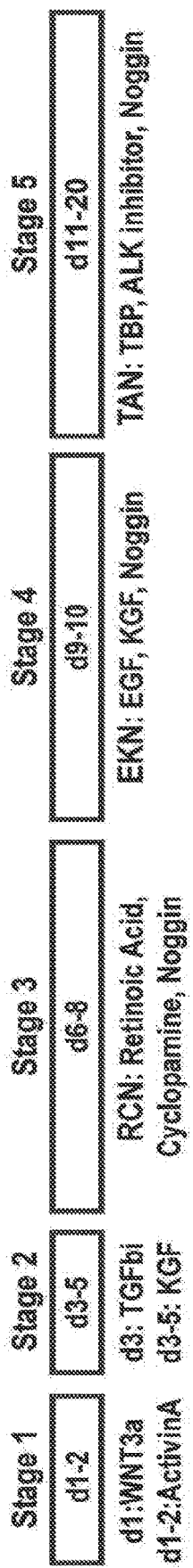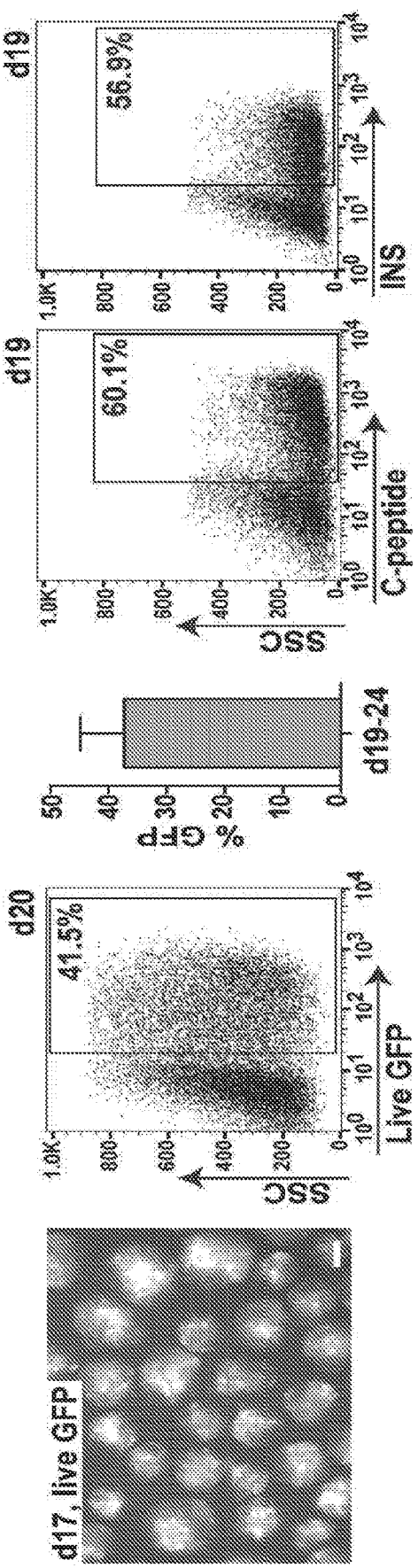

Figure 1F
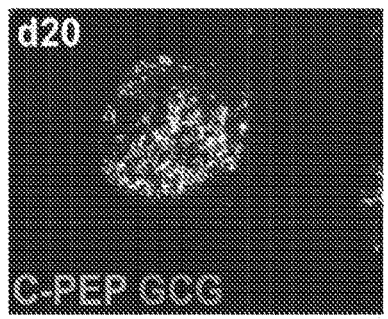
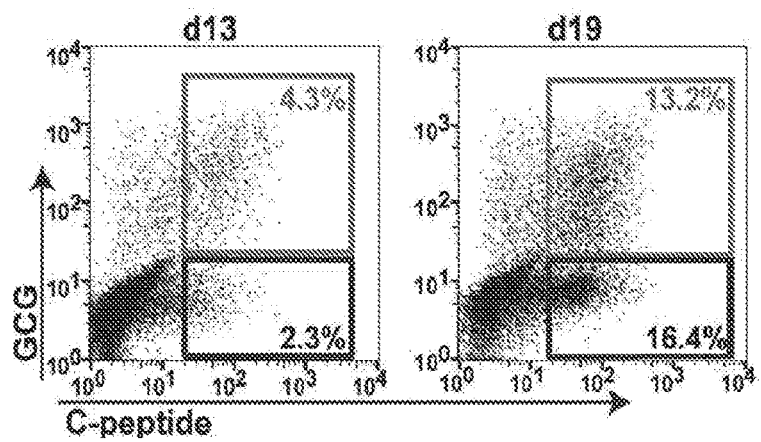
Figure 1G
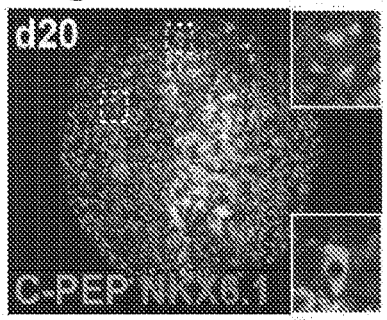
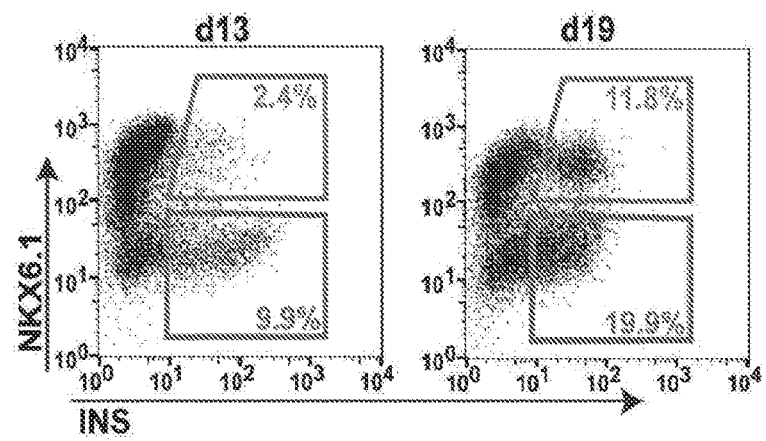
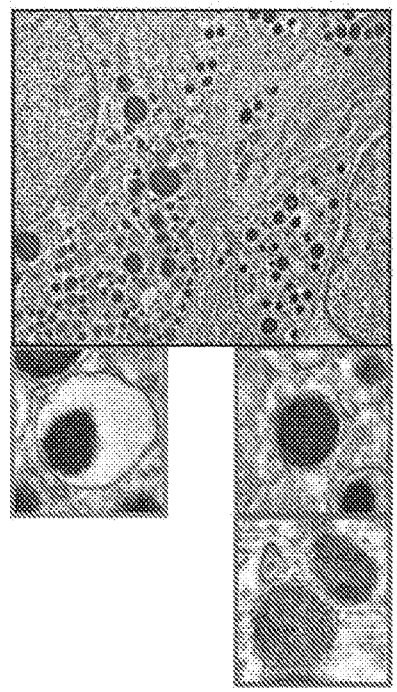
Figure 1H

|  | Factors | |  |
| --- | --- | --- | --- |
| Condition | d6-8 | d9-9.5 |  |
| 1 | Base | Base | Group 1 |
| 2 | C | C | |
| 3 | N | N | |
| 4 | R | R | |
| 5 | RC | RC | |
| 6 | RCN | RCN | |
| 7 | Base | EK | Group 2 |
| 8 | C | EK | |
| 9 | N | EK | |
| 10 | R | EK | |
| 11 | RC | EK | |
| 12 | RCN | EK | |
| 13 | Base | EKN | Group 3 |
| 14 | C | EKN | |
| 15 | N | EKN | |
| 16 | R | EKN | |
| 17 | RC | EKN | |
| 18 | RCN | EKN | |

BASE=B27 only control, R= Retinoic acid, C= Cyclopamine, N= Noggin, E=EGF, K= KGF.

Figure 2A

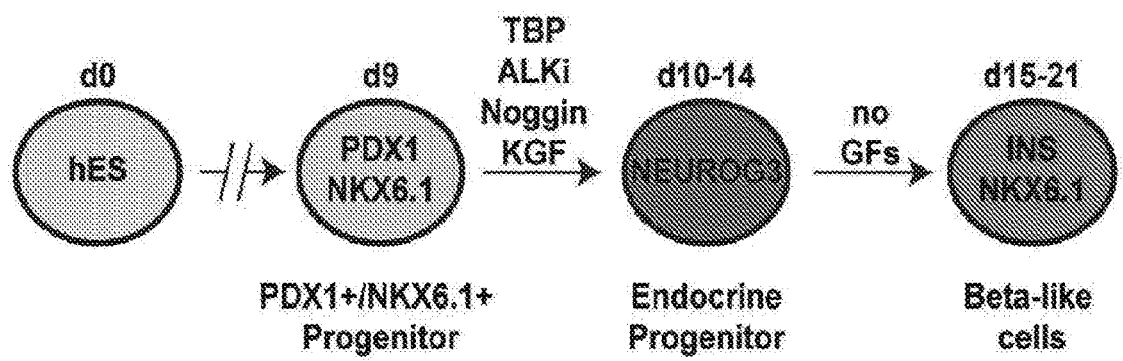
Figure 4A
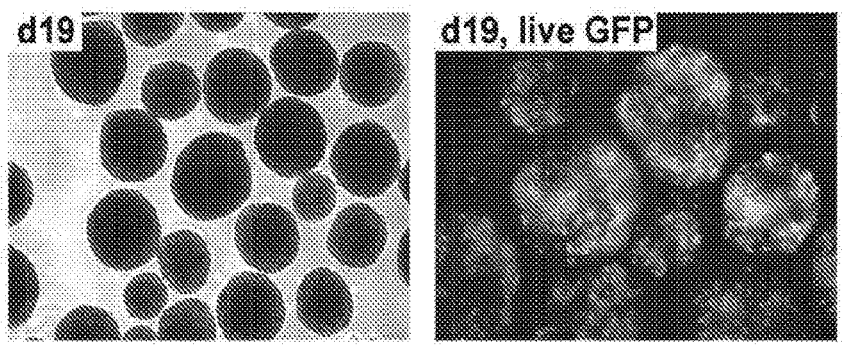 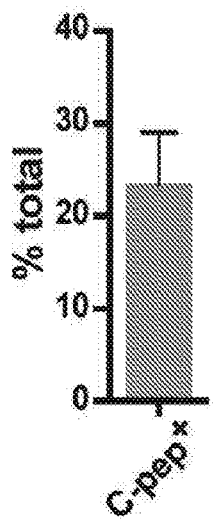
Figure 4B
Figure 4C
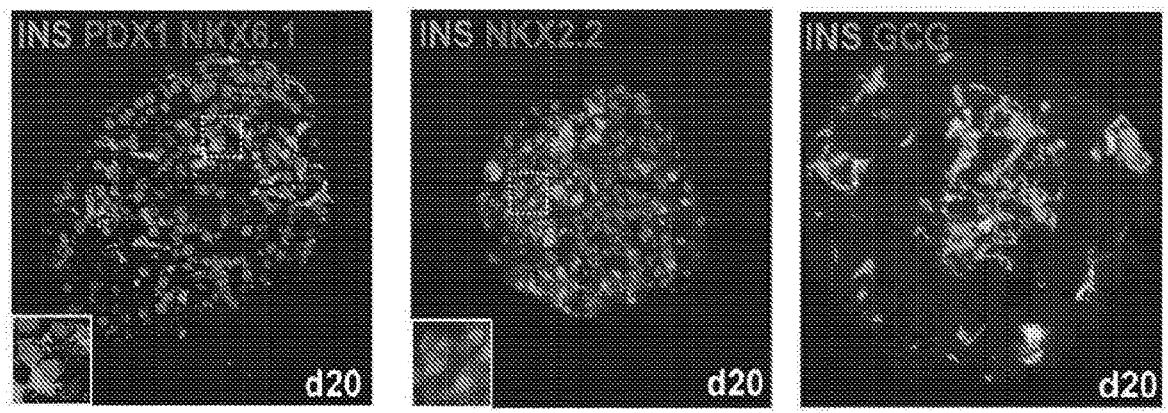
Figure 4D

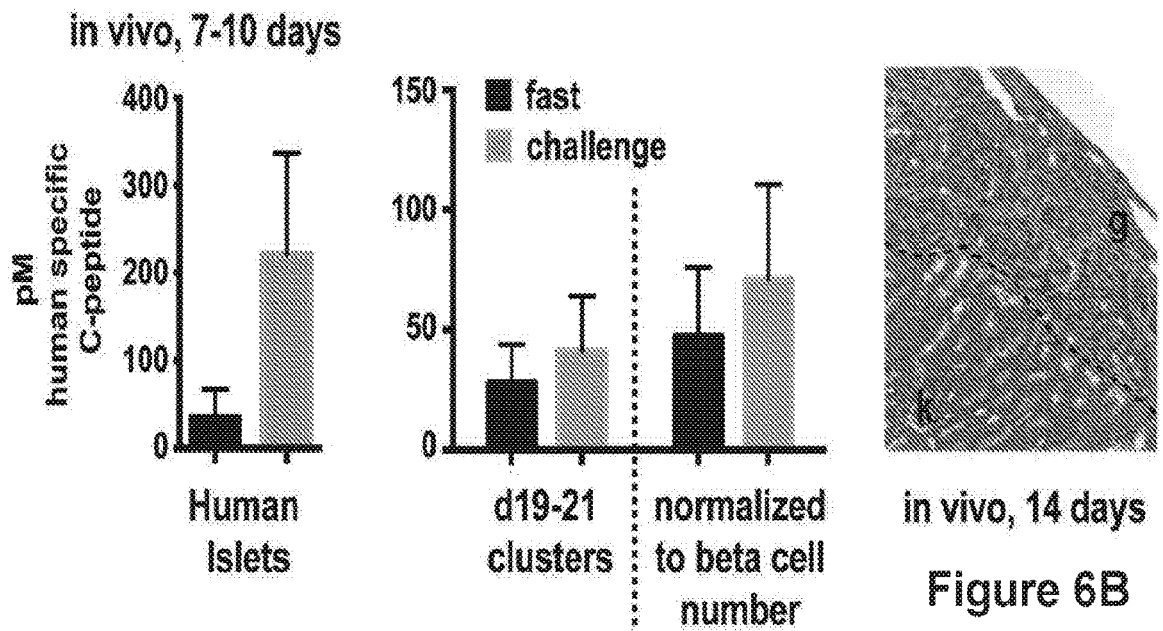
Figure 6A
Figure 6B
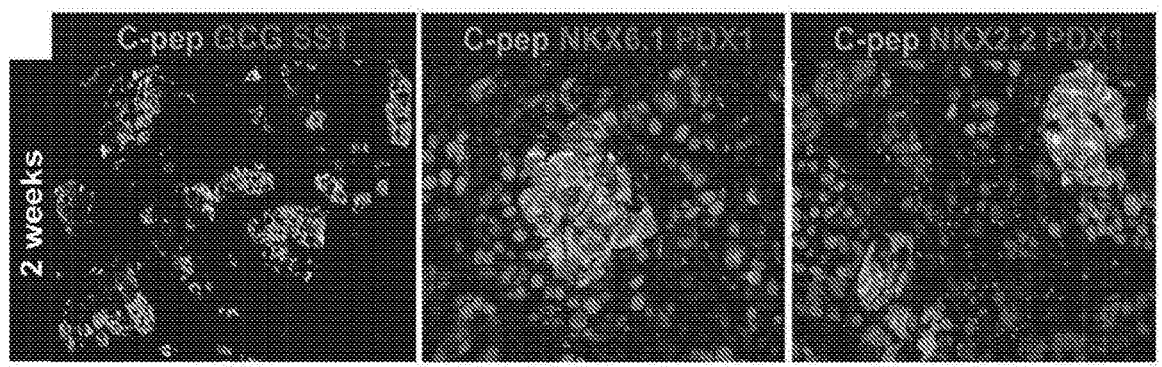
Figure 6C
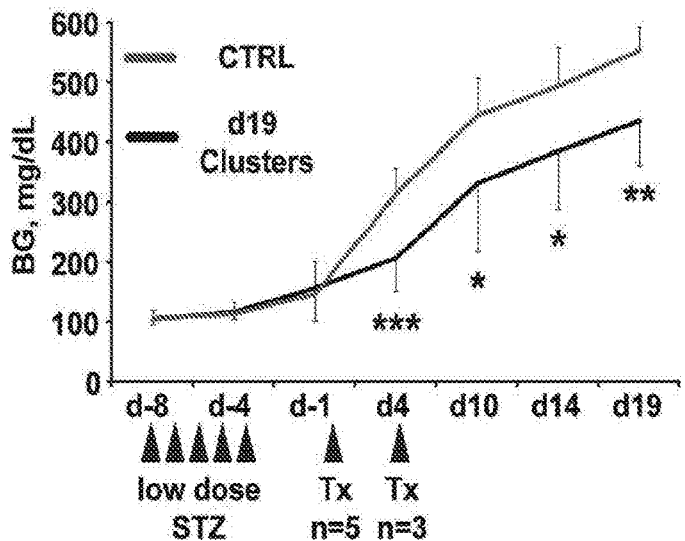
Figure 6D

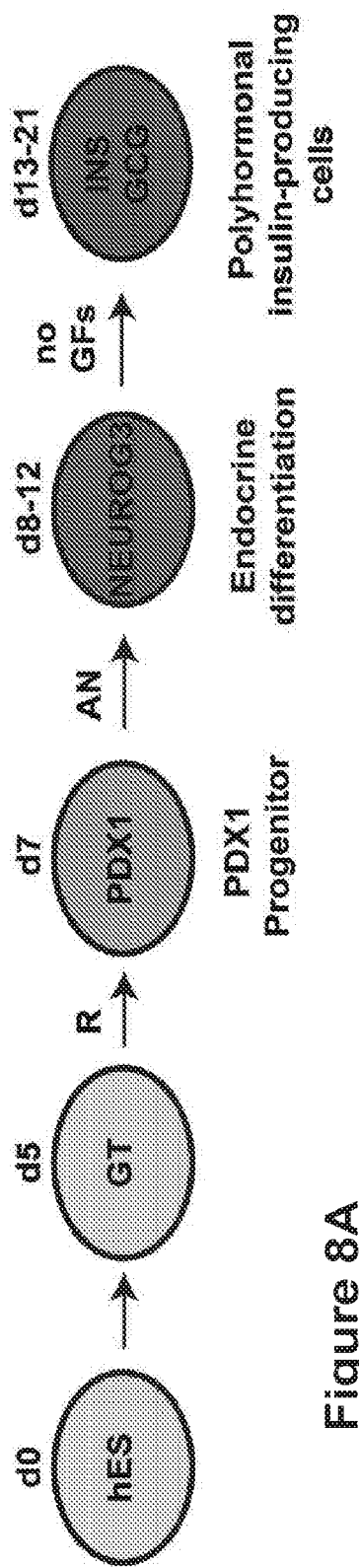
Figure 8A
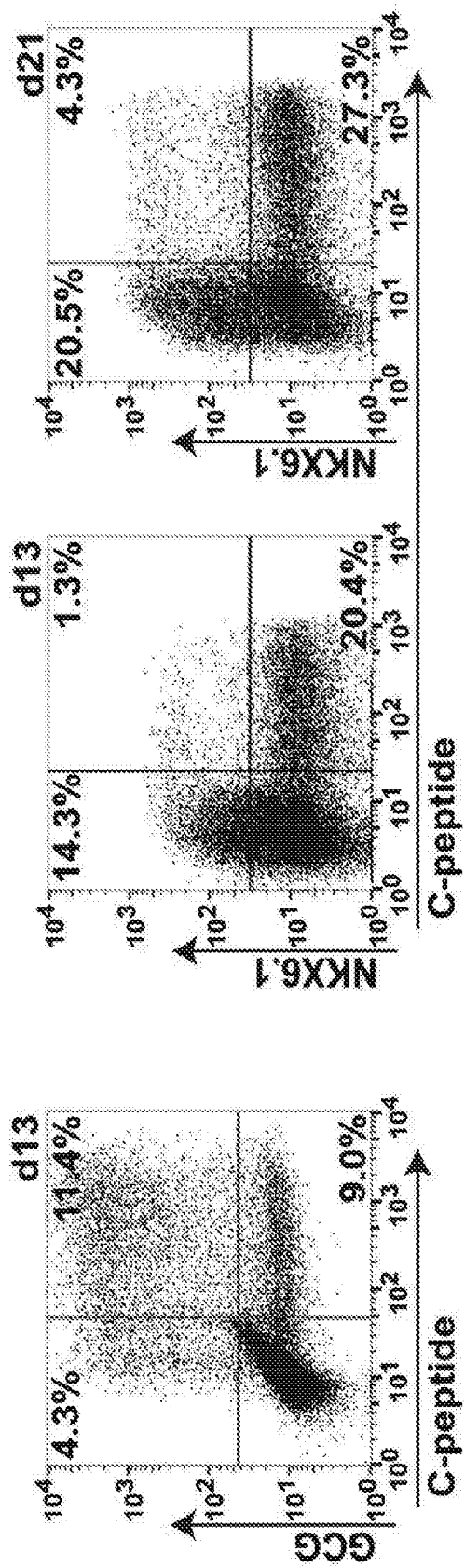
Figure 8C
Figure 8B

CONTROLLED INDUCTION OF HUMAN PANCREATIC PROGENITORS PRODUCES FUNCTIONAL BETA-LIKE CELLS

CROSS-REFERENCE TO RELATED APPLICATION

This application claims the priority benefit under 35 U.S.C. § 119(e) of Provisional U.S. Patent Application No. 62/151,832, filed Apr. 23, 2015, which is incorporated herein by reference in its entirety.

BACKGROUND

Directed differentiation of human pluripotent stem cells into functional insulin-producing beta-like cells holds great promise for cell replacement therapy for patients suffering from diabetes. This approach also offers the unique opportunity to study otherwise inaccessible aspects of human beta cell development and function in vitro.

Diabetes mellitus type 1 and 2 (T1D, T2D) are diseases characterized by autoimmune destruction or progressive dysfunction and subsequent loss of insulin-producing pancreatic beta cells, respectively. Current treatments for both types of patients with diabetes consist of regulating blood glucose levels through injections of exogenous insulin. While this approach provides reasonable management of the diseases, unwanted risks and long-term complications persist due to the inability of tightly maintaining glucose levels within a normal physiological range. Complications include life-threatening episodes of hypoglycemia, as well as long-term complications from hyperglycemia resulting in micro- and macro-angiopathy leading to cardiovascular pathologies and kidney failure, as well as neuropathy. Thus, there is a need for distinct treatments that provide superior control of glucose metabolism to minimize, or ideally eliminate long-term complications.

One existing approach to treating diabetes is transplantation of human cadaveric islet preparations into patients. This procedure typically results in better glycemic control, can render patients insulin independent for prolonged periods of time, and improves overall quality of life (Shapiro et al, 2000; Barton et al, 2012; Posselt et al, 2010). However, the severe shortage of cadaveric organ donors, requirement for lifelong immunosuppression, and variability between islet preparations hampers the use of islet transplantation as a readily available treatment for people with diabetes. Consequently, numerous research efforts have focused on identifying abundant alternative sources of surrogate glucose responsive insulin-producing cells (Hebrok, 2012; Efrat & Russ, 2012; Nostro & Keller, 2012; Tudurí & Kieffer, 2011; Bouwens et al, 2013; Zhou & Melton, 2008; Pagliuca & Melton, 2013). One of the most appealing approaches is the directed differentiation into insulin-producing cells from pluripotent human embryonic stem cells (hESC)(D'Amour et al, 2005; Nostro et al, 2011; Guo et al, 2013b; Van Hoof et al, 2011; Mfopou et al, 2010; Chen et al, 2009; Xu et al, 2011; Shim et al, 2014) and more recently, induced pluripotent stem cells (Maehr et al, 2009; Shang et al, 2014; Hua et al, 2013).

Comprehensive knowledge of signaling events and temporal transcription factor (TF) expression patterns during rodent pancreas organogenesis (Pan & Wright, 2011; Seymour & Sander, 2011; Hebrok, 2003; Murtaugh & Melton, 2003) have accelerated the identification of culture conditions that allow the generation of pancreatic cell types from human pluripotent stem cells (hPSC). Early developmental stages, including definitive endoderm, gut tube-like cells and pancreatic progenitors can be efficiently induced in vitro. Subsequent transitions towards hormone-expressing cells in vitro are less efficient, however, and frequently lead to the formation of a mixed population of different pancreatic progenitors and polyhormonal endocrine cells (Guo et al, 2013a; Nostro et al, 2011; D'Amour et al, 2006). Such polyhormonal cells express insulin among other hormones, but lack expression of key beta cell transcription factors and do not secrete insulin in vitro in response to a glucose challenge—the hallmark function of bona fide beta cells (Guo et al, 2013a; Nostro et al, 2011; D'Amour et al, 2006). Nonetheless, transplantation of such heterogeneous cultures into surrogate mice results in the formation of glucose responsive beta-like cells after several months in vivo (Rezania et al, 2012; Kroon et al, 2008; Szot et al, 2014).

Sophisticated sorting experiments identified progenitor cells expressing Pancreatic and Duodenal Homeobox 1 TF (PDX1, also known as IPF1) and homeobox protein NKX6.1 as the source for these functional beta-like cells (Kelly et al, 2011). While polyhormonal cells have been identified in human fetal pancreas, suggesting that they may reflect aspects of the normal embryonic differentiation process (Riedel et al, 2011; De Krijger et al, 1992), increasing evidence indicates that hESC-derived polyhormonal cells preferentially give rise to single hormone positive alpha-like cells (Rezania et al, 2011). Thus, to fully replicate human beta cell development in vitro, it is imperative to better understand and accurately recapitulate the sequence of embryonic signals required for the proper specification of beta cell precursors, rather than alpha cell precursors.

During normal in vivo pancreatic organogenesis, functional beta cells are generated through a step-wise specification process starting with pancreatic progenitors, identified by the expression of PDX1 (Herrera et al, 2002). While PDX1+ cells can give rise to all pancreatic lineages (Herrera et al, 2002), the subsequent induction of NKX6.1 in these cells restricts their differentiation potential to only endocrine and ductal cells (Schaffer et al, 2010). Endocrine differentiation is then initiated in PDX1+/NKX6.1+ progenitors by short-lived expression of the basic helix loop helix TF Neurogenin 3 (NEUROG3, also known as NGN3) (Gu et al, 2002). Interestingly, the timing of NEUROG3 expression has been shown to be crucial in promoting the formation of diverse endocrine islet cell types (Johansson et al, 2007). For example, precocious induction of endocrine differentiation by forced expression of NEUROG3 in mice results predominantly in the generation of alpha cells (Johansson et al, 2007).

For all of the foregoing reasons, a need continues to exist in the art for materials and methods that provide for the directed differentiation of pluripotent stem cells (e.g., human pluripotent stem cells) into functional insulin-producing beta-like cells for treatment of diabetes.

SUMMARY

Cell therapies utilizing functional insulin-producing beta cells produced from human stem cells hold great promise for the treatment of diabetes. Disclosed herein are data establishing that current pancreatic differentiation protocols induce precocious endocrine differentiation, leading to the formation of undesired polyhormonal endocrine cells. The disclosure further provides a simplified suspension-culture-based differentiation protocol that allows for the correct temporal specification of pancreatic and endocrine progenitors into glucose-responsive beta-like cells in vitro. This approach provides a fast and reproducible supply of functional human beta-like cells and enables detailed investigations into human pancreas development and beta cell biology. Salient features of the technology disclosed herein includes the exclusion of commonly used BMP inhibitors during human embryonic stem cell-to-pancreatic progenitor cell differentiation prevents precocious endocrine induction. Sequential exposure of foregut cells to retinoic acid followed by combined EGF/KGF treatment establishes highly pure PDX1+ and PDX1+/NKX6.1+ progenitor populations, respectively. Precise temporal induction of endocrine differentiation in PDX1+/NKX6.1+ progenitors, but not in PDX1+/NKX6.1− progenitors, results in the generation of functional beta-like cells in vitro. The beta-like cells produced by the disclosed methods exhibit key features of bona fide human beta cells, remain functional after short-term transplantation, and reduce blood glucose levels in diabetic mice.

Elaborating on the preceding observations, current pancreatic progenitor differentiation protocols promote precocious endocrine commitment, ultimately resulting in the generation of non-functional polyhormonal cells. Omission of commonly used BMP inhibitors during pancreatic specification prevents precocious endocrine formation while treatment with retinoic acid followed by combined EGF/KGF efficiently generates both PDX1+ and subsequent PDX1+/NKX6.1+ pancreatic progenitor populations, respectively. Precise temporal activation of endocrine differentiation in PDX1+/NKX6.1+ progenitors produces glucose responsive beta-like cells in vitro that exhibit key features of bona fide human beta cells, remain functional after short-term transplantation, and reduce blood glucose levels in diabetic mice. Thus, our simplified and scalable system accurately recapitulates key steps of human pancreas development, and provides a fast and reproducible supply of functional human beta-like cells.

In one aspect, the disclosure provides a method of generating a PDX1+ progenitor cell comprising contacting an embryonic stem cell with an effective amount of a retinoic acid compound, thereby inducing formation of a PDX1+ progenitor cell. In some embodiments, the embryonic stem cell is a human embryonic stem cell. In some embodiments, the embryonic stem cell is contacted with a retinoic acid compound in vitro. Embodiments are also contemplated that further comprise not contacting the embryonic stem cell with a bone morphogenic protein (BMP) inhibitor prior to expression of NKX6.1 by the cell.

In some embodiments of this aspect of the disclosure, the method further comprises contacting the cell with effective amounts of epidermal growth factor and keratinocyte growth factor, thereby inducing formation of a PDX1+/NKX6.1+ progenitor cell. In some of these embodiments, the cell expresses NKX6.1 prior to the cell contacting at least one of epidermal growth factor and keratinocyte growth factor (K). In some of these embodiments, the cell expresses NKX6.1 prior to contacting epidermal growth factor and keratinocyte growth factor.

In yet other embodiments, the method further comprises inducing the PDX1+/NKX6.1+ progenitor cell to express NEUROG3, resulting in production of an INS+/NKX6.1+ beta-like cell. In some embodiment, the NEUROG3 expression is induced by contacting the PDX1+/NKX6.1+ progenitor cell with an effective amount of bone morphogenic protein, an inhibitor of TGFβ/ALK, or an inhibitor of sonic hedgehog. Embodiments are contemplated wherein the PDX1+/NKX6.1+ progenitor cell is contacted by an effective amount of bone morphogenetic protein and an effective amount of an inhibitor of TGFβ/ALK. In some embodiments, the PDX1+/NKX6.1+ progenitor cell is contacted by an effective amount of bone morphogenetic protein and an effective amount of an inhibitor of sonic hedgehog. In some embodiments, the inhibitor of bone morphogenetic protein is Noggin or the inhibitor of sonic hedgehog is Cyclopamine.

This aspect of the disclosure further comprehends methods wherein the NEUROG3 expression is induced by exposure of the PDX1+/NKX6.1+ progenitor cell to effective amounts of a TATA-Binding Protein, an Activin receptor-Like Kinase inhibitor, Noggin and Keratinocyte Growth Factor, or K. In some embodiments, the NEUROG3 expression begins before expression of NKX2.2 is detected. In some embodiments, no more than 5% of the generated cells are polyhormonal cells. In some embodiments, the INS+/NKX6.1+ beta-like cell is responsive to glucose levels. In some of these embodiments, the INTS+/NKX6.1+ beta-like cell secretes an increased level of insulin in response to an increased glucose level.

Some embodiments of the methods according to the disclosure are provided wherein the INS+/NKX6.1+ beta-like cell does not express a detectable level of the Ki67 marker.

Another aspect of the disclosure is a method for generating an INS+/NKX6.1+ beta-like cell further compromising transplanting the INS+/NKX6.1+ beta-like cell into a human. In some embodiments, the human is diabetic.

Other features and advantages of the disclosure will be better understood by reference to the following detailed description, including the drawing and the examples.

BRIEF DESCRIPTION OF THE DRAWING

FIG. 1. Pancreatic differentiation of hESCs using a large-scale culture system results in two distinct subsets of insulin-producing cells. A: Schematic outlining the differentiation method employed. R=Retinoic acid, C=Cyclopamine, N=Noggin, E=Epidermal growth factor, K=Keratinocyte growth factor, T=TBP, and A=ALK inhibitor. B: Micrograph of MEL1INS-GFP cell clusters after 17 days of differentiation demonstrating strong GFP expression (GFP expression in white). Scale bar=200 μm. C: Flow cytometric analysis at day 20 of differentiation showing 41.5% of all cells expressing GFP under the control of the endogenous insulin promoter. D: Quantification by flow cytometry of the average percentage of GFP+ cells within differentiated cultures after 19-24 days. n=7. Values are average±standard deviation (SD). E: Flow cytometric analysis of intracellular human-specific C-peptide (C-PEP) and insulin (INS) shows comparable percentages of C-PEP and INS positive cells. F: Immunofluorescence staining for C-PEP and glucagon (GCG), and flow cytometric quantification of GCG+/C-PEP+ (red gate), GCG−/C-PEP+ (black gate) populations at days 13 and 19 of differentiation. G: Immunofluorescence staining for C-PEP and NKX6.1, and flow cytometric quantification of NKX6.1+/INS+ (green gate) and NKX6.1−/INS+ (red gate) populations at days 13 and 19. Immunofluorescence insets show two distinct phenotypes for C-PEP+ cells (NKX6.1+ and NKX6.1−). A robust INS/NKX6.1 double positive population is only detected at day 19. H: Transmission electron microscopy of day 20 clusters. Cells contain both secretory vesicles with electron dense cores surrounded by electron light halos (green box), akin to bona fide beta cell vesicles, as well as other granules similar to those found in non-beta pancreatic cells (red boxes).

FIG. 6. Beta-like cells remain glucose responsive after short-term transplantation. A: Levels of circulating human c-peptide measured in sera of mice 7-10 days after transplantation with either 4000 human islets or $5.0\times10^6$ direct-differentiated cells (containing approximately $1.15\times10^6$ beta-like cells). Fasting and challenge sera were collected following an overnight fast and 1 hour after intraperitoneal glucose challenge, respectively. Dashed line separates raw data from serum c-peptide measurements normalized to the number of beta cells present in each human islet graft (4000 human islets transplanted each containing about 1000 cells, approximately 50% of which are beta cells, hence $2.0\times10^6$ beta cells present in grafts total). n=5 for human islets and n=12 for hES-derived grafts. B: Hematoxylin and Eosin staining of day 14 graft. k=kidney, g=graft. Representative data from one of three mice are shown. C: Immunofluorescence staining of differentiated hES grafts 2 weeks post-transplantation for human C-peptide, Glucagon (GCG), Somatostatin (SST), PDX1, NKX6.1, and NKX2.2. Representative data from one of three mice are shown. D: Blood glucose (BG) levels of mice treated with streptozotocin to ablate endogenous beta-cells (STZ) followed by transplantation (Tx) of beta-like cell containing clusters either at day 0 or day 4, as indicated (n=8, two independent differentiation experiments). Values are average±standard deviation. Statistical significance was calculated using two-tailed t-test. $p=*<0.05$, $<0.01$, and $*<0.001$. Control (CTRL)=6-9 animals.

FIG. 8. Induction of NEUROG3 expression in PDX1+ pancreatic progenitors results in insulin-producing cells that lack NKX6.1 expression. A: Schematic outlining the differentiation strategy employed. R=Retinoic Acid, N=Noggin, and A=ALK inhibitor. B and C: Flow cytometric analysis of human c-peptide (C-PEP), glucagon (GCG), and NKX6.1 expression at the indicated differentiation time points. Data representative of 3 to 4 independent experiments with similar results are shown. B: Endocrine differentiation of PDX1+ pancreatic progenitors results in the predominant generation of polyhormonal insulin- and glucagon-producing cells at day 13. C: Insulin-producing cells lack expression of the critical beta cell transcription factor NKX6.1 at day 13 and 21. A small population of NKX6.1+/INS-progenitor cells is generated by NEUROG3-inducing treatment with AN.

DETAILED DESCRIPTION

Given that hESC-derived polyhormonal cells have been shown to give rise to alpha cells (Rezania et al, 2011), we expected the in vitro generation of polyhormonal endocrine cells to result from premature assignment to the endocrine fate. To address this issue, a detailed step-wise analysis of pancreatic progenitor generation and endocrine induction was performed. Most current protocols efficiently establish PDX1+ progenitors by using Retinoic Acid in combination with molecules to inhibit bone morphogenic protein (BMP) and sonic hedgehog (SHH) signaling pathways, while simultaneously adding either fibroblast growth factor 10 or keratinocyte growth factor (KGF, also known as FGF7) (Rezania et al, 2012; Hua et al, 2013; Guo et al, 2013b; Nostro & Keller, 2012; Mfopou et al, 2010). Disclosed herein is the need to temporally control the introduction of inducing agents in the pathway of directed differentiation of embryonic stem cells to functional beta-like pancreatic cells. For example, the early or indiscriminate use of BMP inhibitors to specify pancreatic cells promotes the precocious induction of endocrine differentiation in PDX1+ pancreatic progenitors, which results in the formation of polyhormonal cells. BMP inhibitors do have a role in directed differentiation of ES cells to beta-like cells, but only if the inhibitors are introduced later in the process, i.e., after the cells have begun to express NKX6.1. Simplified culture conditions have been identified that replicate fetal endocrine development and allow for the precise and efficient generation of PDX1+ and PDX1+/NKX6.1+ progenitor populations without precocious activation of the endocrine marker NEUROG3. Subsequent induction of endocrine differentiation in correctly specified PDX1+/NKX6.1+ progenitor cells results in the formation of glucose-responsive insulin-expressing beta-like cells in vitro within, or less than, three weeks. Our study, therefore, details a simplified directed differentiation protocol that closely recapitulates key aspects of human endocrine development and results in the formation of large numbers of glucose-responsive beta-like cells under cell culture conditions.

Figure 11:
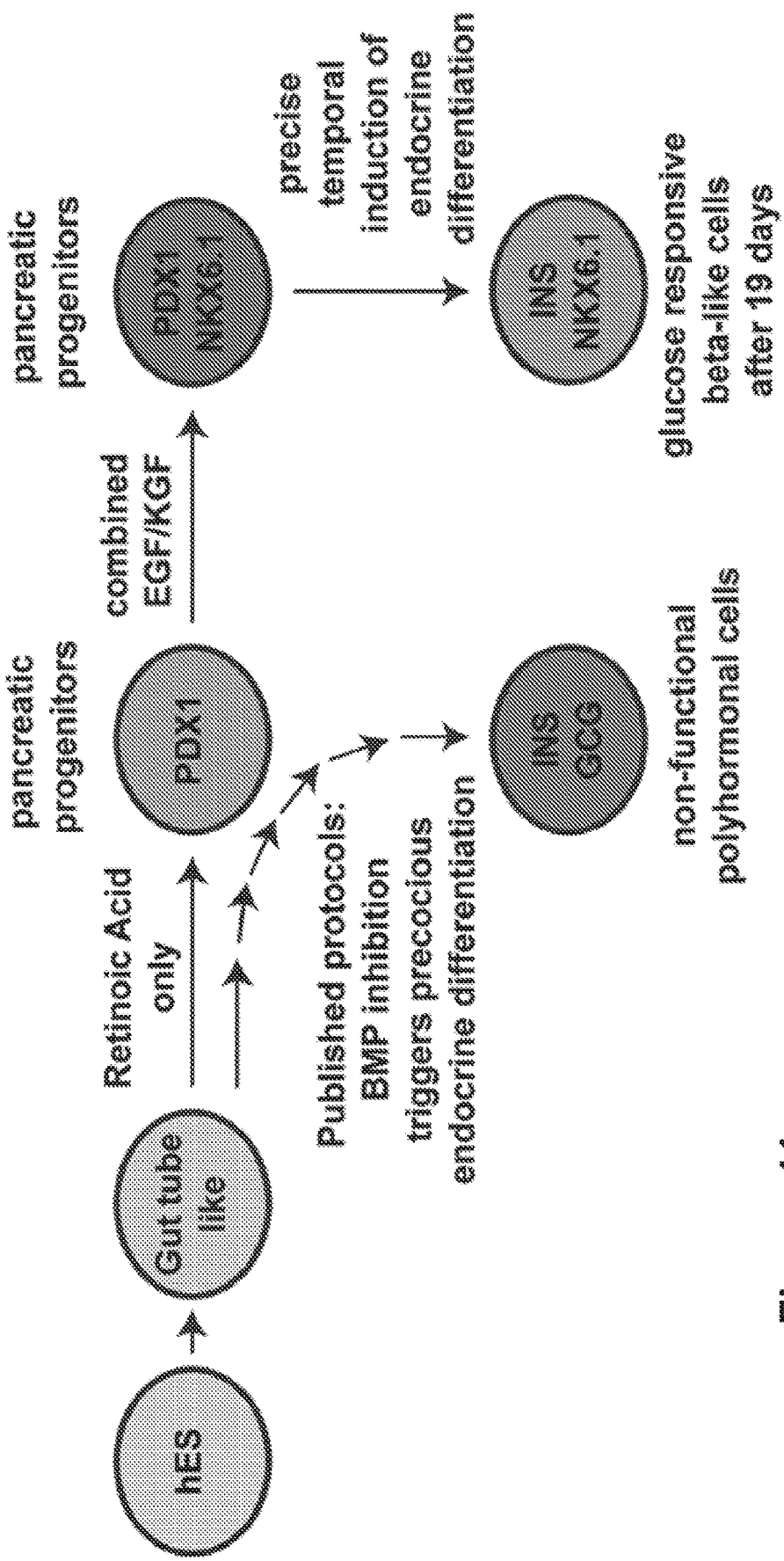
FIG. 11. Schematic comparative illustration of pancreatic cell (e.g., beta islet cell) directed differentiation protocols known in the art and disclosed herein. Provided is an illustration comparing directed differentiation protocols for eliciting differentiation of human embryonic stem cells (hES) to pancreatic cells such as beta islet cells. Conventional protocols proceed from hES through foregut to the column in the center of the Figure proceeding through PDX1 to NGN3 and then to INS GCG. The methodology disclosed herein proceeds from hES through foregut, PDX1, PDX1/NKX6.1, NGN3, and then to INS NKX6.1.

A simplified differentiation protocol is disclosed herein that replicates key steps of embryonic pancreas organogenesis for the defined generation of human pancreatic progenitor and endocrine cell types from human embryonic stem cells (hESCs) that results in the formation of glucose-responsive beta-like cells in vitro. A straightforward schematic comparing the protocol disclosed herein to conventional protocols is provided in FIG. 11. hESC derived beta-like cells exhibit key features of cadaveric human beta cells both in vitro and in vivo, most notably their ability to respond to physiological increases in glucose concentrations by secreting insulin. Gene expression analysis of beta-like cells indicates the presence of factors essential for beta cell function, proper biosynthesis of mature insulin, glucose metabolism, and insulin secretion at levels comparable to human islets. In addition, beta-like cells display ultrastructural features of bona fide human beta cells, such as appropriate secretory vesicles. Thus, critical elements necessary for the generation and appropriate processing, packaging and storing of insulin in its bioactive mature form are present in these hESC-derived cells. Finally, beta-like cells remained functional after short-term transplantation and reduced blood glucose levels in a murine model of diabetes, further confirming the correct differentiation state of the cells.

Recently, two other groups have reported the derivation of glucose responsive beta-like cells from hESC cells that share many characteristics of the beta-like cells described herein (Rezania et al, 2014; Pagliuca et al, 2014). Both of these studies, however, focused on optimizing the later stages of direct differentiation, while employing parts of published protocols, namely the addition of RCN, to establish pancreatic progenitor populations. Data disclosed herein demonstrate that generation of pancreatic progenitors using this method also results in the undesirable generation of immature polyhormonal endocrine cells that lack expression of the critical beta cell transcription factor NKX6.1. Indeed, both published studies do note appreciable populations of C-peptide/insulin positive cells that lack NKX6.1 expression. We demonstrate that polyhormonal cells result from precocious endocrine induction in PDX1+ pancreatic progenitors (lacking NKX6.1 expression), which can be avoided by omitting BMP inhibitors during the pancreas specification stage. Further, our detailed analysis of the effects of individual RCN factors on expression of key pancreatic markers revealed that retinoic acid alone is sufficient to induce proficient generation of more than 98% PDX1+ pancreatic progenitors. Subsequent exposure to EGF and KGF results in the rapid and effective activation of NKX6.1 in these cells, generating PDX1+/NKX6.1+ progenitor cells with the ability to give rise to beta-like cells in vitro. These simplified differentiation conditions enable the efficient generation of human pancreatic and more restricted endocrine progenitor populations from pluripotent stem cells without unwanted formation of polyhormonal cells. This simplified differentiation protocol more closely resembles key aspects of early human pancreas development and, as such, represents an improvement over published protocols.

Studies in rodents have shown an important role for Notch signaling in the endocrine differentiation of progenitor cells in vivo. While initially required for the generation of competent progenitor cells, a subsequent reduction of Notch signaling is necessary for the induction of NEUROG3 expression that initiates endocrine differentiation (Shih et al, 2012). In the context of in vitro differentiation, previous studies have shown that direct inhibition of Notch signaling by gamma secretase inhibitors or the use of BMP and TGFβ/ALK inhibitors results in increased insulin expression at later stages (Mfopou et al, 2010; Nostro et al, 2011; Pagliuca et al, 2014; Rezania et al, 2014). We employed BMP and Activin receptor-Like Kinase (ALK) inhibition over a 5-day window to induce NEUROG3 expression specifically in PDX1+/NKX6.1+ progenitors, which resulted in the efficient generation of INS+/NKX6.1+ beta-like cells, while only few polyhormonal cells were observed (about 3%, which is less than 5%) Likely, these unwanted cells originated from the small percentage of PDX1 pancreatic progenitors present at the time of endocrine induction. In contrast to the formation of PDX1+ and PDX1+/NKX6.1+ progenitors that occurs rapidly (36-48 hours after addition of inducing factor(s)) and uniformly in the majority of cells, endocrine differentiation occurs over a prolonged period and is confined to a small subset of total cells. This might be a reflection of the situation observed during normal human pancreas development, where only few progenitor cells initiate the endocrine differentiation program at any given time (Jennings et al, 2013). While simultaneous widespread induction of endocrine differentiation in a majority of PDX1+/NKX6.1+ progenitor population would greatly reduce differentiation time and increase beta-like cell yield, our results point to a regulation of NEUROG3 expression that requires subtle, yet temporally precise, adjustment that appears more complex than just Notch inhibition. As our differentiation protocol allows for a tight control of NEUROG3 expression, it could be used in future studies to identify novel regulators of NEUROG3 gene expression, and ideally to achieve uniform NEUROG3 activation during direct differentiation in vitro.

While cadaveric islet preparations are widely accepted as the gold standard for studying human beta cells, several problems associated with their use remain. For example, their performance and utility depend on a number of confounding factors: genetic variance, age and life style of the donor, isolation time, islet purity and shipping conditions. By eliminating the constraints of availability and reproducibility, we expect hESC-derived beta-like cells to provide an important therapeutic and a tool to accelerate understanding of the biology of human beta cells.

Taken together, our fast and simplified protocol provides precise temporal control over the generation of subsequent pancreatic progenitor and endocrine cell types and results in the establishment of human beta-like cells that exhibit glucose responsiveness in vitro and in vivo. Our suspension-based direct differentiation approach is scalable, and our ability to produce large numbers of beta-like cells will further accelerate efforts to efficiently deliver a safe and effective cell therapy to patients suffering from diabetes. Furthermore, through the production and maintenance of different developmental cell populations, our approach can be used for more detailed investigations into human pancreas development and human beta cell function that were previously impossible due to limited donor material, such as large scale drug screens and genome-wide gene function studies.

The following examples illustrate embodiments of the disclosure.

Example 1

Materials and Methods

Cell Culture

Undifferentiated MEL1 INS$^{GFP/W}$ reporter cells (Micallef et al, 2012) were maintained on mouse embryo fibroblast feeder layers (Millipore) in hESC media as described (Guo et al, 2013b). Suspension-based differentiations were carried out as follows. Briefly, confluent cultures were dissociated into single cell suspension by incubation with TrypLE (Gibco). Cells were counted and each well of 6-well low-adherence plates were seeded with $5.5 \times 10^6$ cells in 5.5 ml hES media supplemented with 10 ng/ml Activin A (R&D systems) and 10 ng/ml HeregulinB1 (Peprotech). Plates were placed on an orbital shaker at 100 rpm to induce sphere formation, as described (Schulz et al, 2012). To induce definitive endoderm differentiation, aggregates were collected 24 hours later in a 50 ml falcon tube, allowed to settle by gravity, washed once with PBS and re-suspended in d1 media (RPMI (Gibco) containing 0.2% FBS, 1:5000 ITS (Gibco), 100 ng/ml Activin A, and 50 ng/ml WNT3a (R&D systems)). Clusters from 3 wells were combined into 2 wells at this point and distributed into fresh low-attachment plates in 5.5 ml d1 media. Media thereafter was changed daily, by removing either 4.5 ml media (at the end of d1) or 5.5 ml media the following days and adding back 5.5 ml fresh media until day 9. After day 9, only 5 ml of media was removed and added daily.

Differentiation employing published protocols has been described (Schulz et al, 2012; Rezania et al, 2012). Media in our simplified differentiation protocol consists of, d2: RPMI containing 0.2% FBS, 1:2000 ITS, and 100 ng/ml Activin A; d3: RPMI containing 0.2% FBS, 1:1000 ITS, 2.5 µM TGFbi IV (CalBioChem), and 25 ng/ml KGF (R&D systems); d4-5: RPMI containing 0.4% FBS, 1:1000 ITS, and 25 ng/ml KGF. d6-7: DMEM (Gibco) with 25 mM Glucose containing 1:100 B27 (Gibco), 3 nM TTNBP (Sigma); d8: DMEM with 25 mM Glucose containing 1:100 B27, 3 nM TTNBP, and 50 ng/ml EGF (R&D systems); d9: DMEM with 25 mM Glucose containing 1:100 B27, 50 ng/ml EGF, and 50 ng/ml KGF. d10-14: DMEM with 25 mM Glucose containing 1:100 B27, 500 nM LDN-193189 (Stemgent), 30 nM TATA-Binding Protein (TBP; Millipore), 1000 nM Alki II (Axxora), and 25 ng/ml KGF; d15-21: DMEM with 2.8 mM Glucose containing 1:100 Glutamax (Gibco) and 1:100

NEAA (Gibco). Human islets were from Prodo Laboratories or the UCSF Islets and Cellular Production Facility.

Mice

NOD.Cg-Prkdcscid Il2rgtm1 Wjl/SzJ mice (NSG) were obtained from Jackson Laboratories. Mice used in this study were maintained according to protocols approved by the University of California, San Francisco Committee on Laboratory Animal Resource Center. For kidney capsule grafts, approximately $5.0 \times 10^6$ hESC differentiated cells in spheres and 4000 human islet equivalents were transplanted as described (Russ & Efrat, 2011; Szot et al, 2007). For glucose-induced insulin secretion, mice were fasted overnight and serum was collected before and after intraperitoneal administration of 3 g/kg D-glucose solution. For induction of diabetes, mice were administered 35 mg/kg streptozotocin via intraperitoneal injection for 5 days. Graft bearing kidneys were removed for immunofluorescence analysis. No statistical method was employed to determine sample size, mice were not randomized and analysis was not blinded.

Cell Sorting and Flow Cytometric Analysis

Briefly, spheres were collected and allowed to settle by gravity. Clusters were washed once in PBS and dissociated by gentle pipetting after 12-15 minutes incubation in Accumax (innovative cell technologies). For sorting, cell suspension were filtered and re-suspended in FACS buffer consisting of phosphate-buffered saline (PBS) (UCSF cell culture facility) containing 2 mM EDTA (Ambion) and 1% BSA (Sigma). Dead cells were excluded by DAPI (Sigma) staining. Cell sorting was performed on a FACS Aria II (BD Bioscience). For flow-based analysis, dissociated cells were fixed with 4% paraformaldehyde (Electron Microscopy Science) for 15 minutes at room temperature, followed by two washes in PBS. Samples were either stored at 4 C or immediately stained with directly conjugated antibodies. Data analysis was performed with FlowJo software. Mouse Glucagon and mouse human C-peptide antibodies were conjugated in-house by the UCSF Antibody Core and/or with Antibody Labeling Kits (Molecular Probes) according to manufacturer's instructions. Commercially available directly conjugated antibodies, i.e., antibodies Human PAX6-Alexa647, Islet-1-PE, NKX6.1-Alexa647, NKX6.1-PE, ChromograninA-PE, NeuroD1-Alexa647, PDX1-PE, and Ki67-Alexa647, were from BD Bioscience.

Electron Microscopic Analysis

Spheres were fixed by adding 37° C. 0.1M sodium cacodylate solution (Sigma) containing 2% paraformaldehyde (Electron Microscopy Science) and 2.5% glutaraldehyde (Electron Microscopy Science), 3 mM $CaCl_2$ (Sigma), final pH 7.4. Spheres were then transferred to 4° C. for approximately 18 hours, followed by standard processing and analysis by the Electron Microscope Lab/Diabetes Center Microscope Core.

Immunofluorescence Analysis

Spheres were fixed for 15-30 minutes at room temperature with 4% paraformaldehyde, followed by multiple washes in PBS. Whole mount staining was performed in suspension, by first blocking overnight at 4° C. in blocking buffer consisting of CAS-block (Invitrogen) with 0.2% TritonX (Fisher). Primary antibodies were incubated overnight at 4° C. in blocking buffer, followed by washes in PBS containing 0.1% Tween-20 (PBS-T, Sigma) and incubation in appropriate secondary antibodies diluted in PBS-T overnight at 4° C. The next day, clusters were washed in PBS-T followed by PBS and mounted with Vectashield (Vector) on glass slides. For sectioning of clusters, spheres were embedded in 2% Agar (Sigma), followed by dehydration, paraffin embedding, and sectioning. Cut sections were rehydrated and treated with an antigen retrieval solution (Biogenex) before incubation with primary antibodies overnight at 4° C. in blocking buffer. The next day, sections were washed 3 times in PBS-T and incubated with appropriate secondary antibodies for 30-40 minutes at room temperature in PBS-T. Appropriate Alexa-conjugated secondary antibodies were purchased from JAX or Molecular Probes and used at 1:500 dilutions. Slides were washed in PBS-T and PBS before mounting in Vectashield. Nuclei were visualized with DAPI. Images were acquired using a Leica SP5 microscope or a Zeiss ApoTome. Primary antibodies were employed as follows:

| Antigen | Species | Dilution | Manufacturer |
| --- | --- | --- | --- |
| Human C-peptide | Mouse | 1:200 | Chemicon |
| Human C-peptide | Rat | 1:1000 | DSHB |
| Insulin | Mouse | 1:1000 | Sigma |
| Insulin | Guinea pig | 1:500 | DAKO |
| Glucagon | Mouse | 1:1000 | Sigma |
| NKX6.1 | Mouse | 1:100 | DSHB |
| NKX2.2 | Mouse | 1:20 | DSHB |
| PDX1 | Goat | 1:200 | R&D systems |
| Human NEUROG3 | Sheep | 1:300 | R&D systems |
| Ki67 | Rabbit | 1:100 | NovoCastra | qPCR Analysis

Total RNA was isolated with TRIZOL (Sigma) or micro/mini RNAeasy kit (Qiagen) and reverse transcribed using the iScript cDNA Kit (Bio-Rad) according to manufacturer's instructions. qPCR analysis was performed on an ABI 7900 HT Fast Real-Time PCR System (Applied Biosystems) and CFX Connect Real Time System (Biorad) using standard protocols. Primers were Taqman Probes (Applied Biosystems) and/or as published previously (Liu et al, 2014). P-values were calculated using a two-tailed student's t-test.

Content Analysis

Insulin, human C-peptide and proinsulin analyses were performed by measuring an aliquot of acidic ethanol lysed clusters with commercially available ELISA kits (Insulin Cat. 80-INSMR-CH10, human C-peptide cat. 80-CPTHU-CH01, and proinsulin Cat. 80-PINHUT-CH01; all from Alpco). Total DNA was quantified by PicoGreen (Invitrogen) assay and normalized to the percentage of C-peptide-positive cells in each sample.

Western Blotting for Proinsulin/Insulin:

Cell lysates were resolved on 4-12% acrylamide gradient SDS-PAGE gels (NuPAGE, Invitrogen) normalized to cellular DNA (Quant-iT dsDNA, Molecular Probes). The samples were then electrotransferred to nitrocellulose membranes and immunoblotted with guinea pig anti-insulin, which recognizes both proinsulin and insulin, as previously described (Haataja et al, 2013). Immunoblotting with anti-tubulin was used as a confirmatory loading control. HRP-conjugated secondary antibodies (Jackson ImmunoResearch) were used for enhanced chemiluminescence detection (Millipore). The analysis was performed four times with isolated human islets used as a positive control.

Glucose Stimulated Insulin Secretion

Human islets or hES-derived spheres were transferred into tubes and washed twice with Krebs-Ringer Bicarbonate buffer (KRB) containing 2.8 mM Glucose. Samples were incubated for one hour in 2.8 mM glucose containing KRB to allow equilibration of cells. The 2.8 mM buffer was removed and replaced with fresh KRB containing 2.8 mM glucose for one hour followed by incubation for another hour in KRB containing 16.7 mM glucose. After the incubation period, buffers were collected for human C-peptide-specific ELISA analysis using a commercially available kit (Alpco).

Example 2

Pancreatic Differentiation of hESCs Using a Large-Scale Culture System Results in Two Distinct Subsets of Insulin Producing Cells.

To generate pancreatic beta-like cells from human PSC, we established a scalable three-dimensional suspension culture system based on previously reported methods (Schulz et al, 2012; Rezania et al, 2012) (FIG. 1A). To monitor the generation of live insulin-producing cells and facilitate their isolation, we employed the recently published INS$^{GFP/W}$ reporter cell line (Micallef et al, 2012) in which green fluorescence protein (GFP) expression is under the control of the endogenous insulin promoter. Using this differentiation protocol, GFP reporter expression was readily observed at day 13 and increased thereafter, resulting in an average of 37±8% GFP positive cells between days 19-24 (FIG. 1B-D). The validity of GFP as an accurate substitute for insulin was verified by staining with an insulin-specific antibody, which revealed an even higher percentage of insulin-producing cells (up to 60%) likely due to delayed accumulation of the fluorescence marker (FIG. 1E). Similar results were obtained with an antibody specific to human C-peptide, excluding antibody reactivity due to insulin uptake from culture media (FIG. 1E). Co-staining for human C-peptide and glucagon (GCG), a hormone normally produced by alpha cells, showed that 4.3% and 13.2% of all cells exhibited a polyhormonal phenotype at day 13 and day 19, respectively (FIG. 1F). Co-staining for C-peptide and NKX6.1 at day 20 indicated the presence of some double positive beta-like cells (FIG. 1G). Quantitative flow cytometry analysis revealed that the proportion of INSULIN and NKX6.1 double-positive beta-like cells increased from less than 2.5% at day 13 to approximately 12% cells at day 19 of total cells (FIG. 1G). Ultrastructural analysis of differentiated cultures showed cells containing secretory vesicles with an electron dense core surrounded by an electron light halo (FIG. 1H), a morphology reminiscent of insulin vesicles that are found in human beta cells. The majority of cells, however, exhibited a mixture of secretory granules usually found in non-beta cells of human pancreas preparations (FIG. 1H). Thus, differentiation experiments employing published protocols (Schulz et al, 2012; Rezania et al, 2012) result in the efficient generation of two distinct insulin-producing cell populations: INS+ cells that do not co-express the critical TF NKX6.1 and manifest as polyhormonal cells, and INS+/NKX6.1+ beta-like cells that more closely resemble human beta cells. Notably, INS+/NKX6.1+ beta-like cells are absent from cultures at earlier time points but appear and increase in number at later stages of differentiation, indicating that they are derived from a distinct progenitor cell type.

Example 3

Defining the Temporal Activities of Individual Signaling Factors to Efficiently Generate PDX1+ and PDX1+/NKX6.1+ Pancreas Progenitor Populations while Preventing Precocious Induction of Endocrine Differentiation.

Figure 2B:
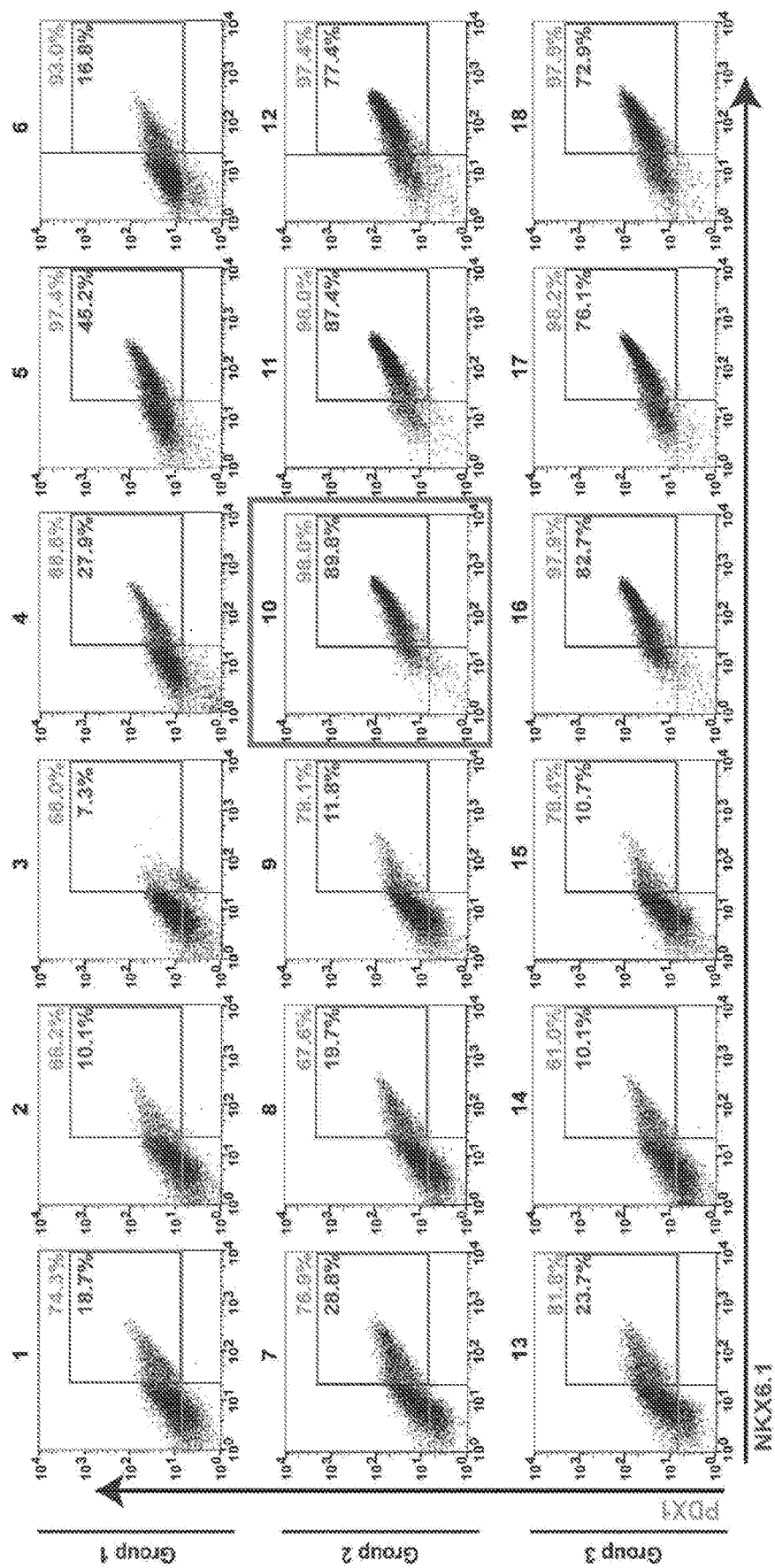
FIG. 2. Defining the temporal activities of individual signaling factors to efficiently generate PDX1+ and PDX1+/NKX6.1+ pancreas progenitor populations while preventing precocious induction of endocrine differentiation. A-C: Pancreatic progenitor marker expression at day 9.5 after treatment with conventional differentiation factors alone or in different combinations. Treatments consisted of combinations of Cyclopamine (C), Noggin (N), and retinoic acid (R) during days 6-8, followed by subdivision of each condition into three treatment groups during day 9-9.5. Group 1) continuation of day 6-8 treatment; Group 2) treatment with EGF and KGF (EK); Group 3) treatment with EGF, KGF, and Noggin (EKN). The condition selected for further studies, '10', is marked with a green box. Data shown are representatives of results obtained in two independent experiments. A: Table detailing 18 different culture conditions that were evaluated. B: Quantification of PDX1 (orange gate) and NKX6.1 (blue gate) protein expressing cells in individual conditions after 9.5 days of differentiation. C: NKX6.1 and NEUROG3 protein expression assessed by whole mount staining of differentiated clusters at 9.5 days. Note robust NEUROG3 expression in all clusters exposed to N (conditions 3, 6, 9, and 12-18).
Figure 2C:
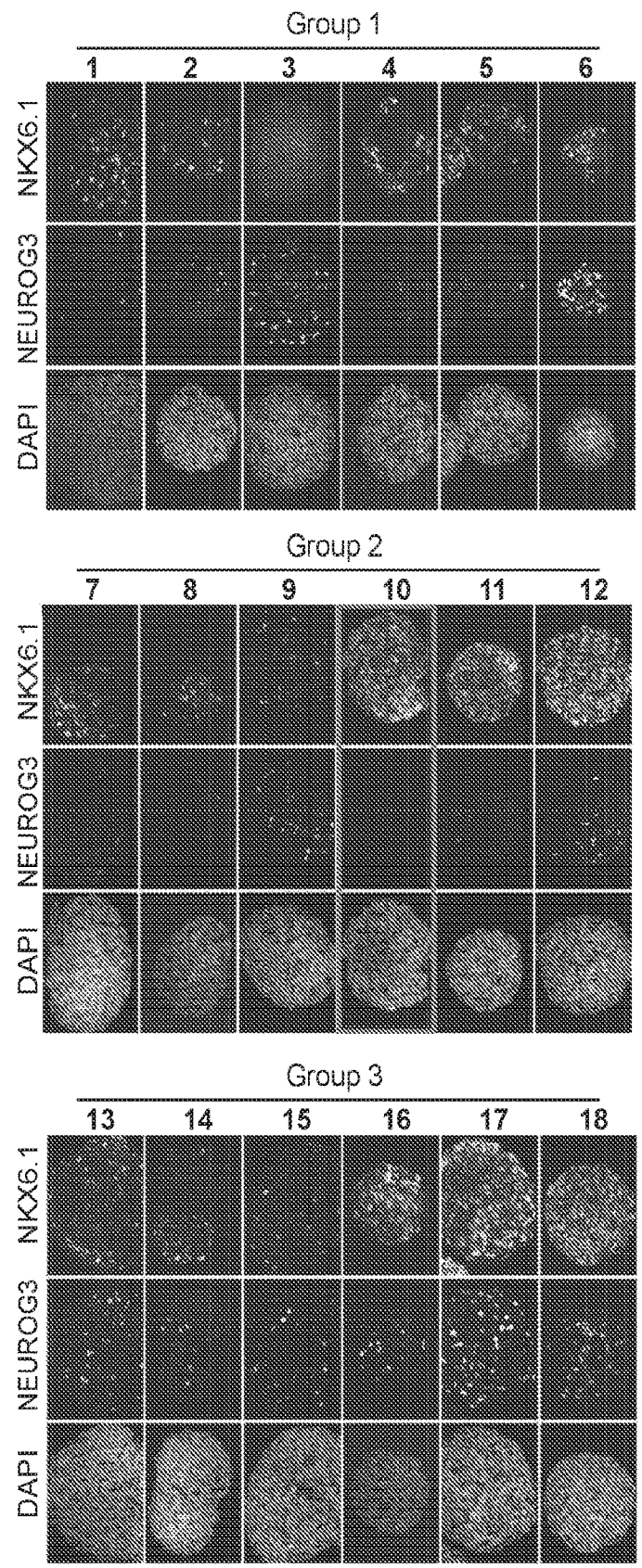

To characterize the type of progenitors present in differentiating cultures at the point of endocrine induction, we performed a detailed time course analysis for the expression of pancreatic markers PDX1, NKX6.1, NEUROG3, GCG and INS (FIG. 7). High expression of the progenitor marker PDX1 was efficiently induced and maintained starting one day after the combined addition of Retinoic Acid (R), the SHH inhibitor Cyclopamine (C), and the BMP inhibitor Noggin (N) to the culture media (referred to as RCN, Day 6, FIGS. 7A and B). Subsequent treatment with epidermal growth factor (EGF), KGF and N (EKN) resulted in the robust generation of PDX1+/NKX6.1+ double positive cells reaching 67% of the total population at day 11 (FIGS. 7A and B). Immunofluorescence analysis revealed that the RCN cocktail of factors widely used to generate pancreatic endoderm also induces precocious expression of NEUROG3 in PDX1+ pancreatic progenitors. Indeed, the expression of NEUROG3 can be detected as early as day 6, when NKX6.1 protein is absent from all cells (FIGS. 7A and B). Consequentially, insulin-expressing cells that are first detected 4 days after NEUROG3 induction (starting at day 10), do not co-express NKX6.1 and are mostly polyhormonal (FIGS. 1F and G, and FIG. 7C). In contrast, INS/NKX6.1 double positive beta-like cells can be readily detected only at later time points (day 19, FIG. 1G), indicating that these cells differentiate from PDX1/NKX6.1 double positive progenitor cells. We thus expected that robust generation of PDX1+/NKX6.1+ progenitor cells prior to induction of NEUROG3 would allow efficient generation of beta-like cells in vitro. To determine which of the factors used between days 6-8 in the original protocol (R, C, and N) were responsible for the induction of PDX1, NKX6.1 and NEUROG3, we incubated spheres with each of the factors alone or in different combinations over days 6-8 (FIG. 2A). Basal media with B27 but lacking any additional factors served as the control condition. At the end of day 8, each of these six conditions was further subdivided into three different treatment groups: media composition remained the same as during days 6-8 (group 1), or were changed either to EK (group 2), or to EKN (group 3), resulting in 18 individual experimental conditions (FIG. 2A). Spheres cultured under each condition were analyzed at day 9.5 by flow cytometry to quantify the expression of PDX1 and NKX6.1, and by conventional immunofluorescence analysis for NKX6.1 and NEUROG3 expression. As shown in FIG. 2B, spheres within group 1 that had been exposed to retinoic acid during days 6-8, either alone or in combination with other factors (conditions 4, 5, and 6), exhibited highly efficient generation of PDX1 positive progenitors (>88%), while addition of C or N alone (conditions 2 and 3) did not result in enhanced generation of PDX1+ cells over base media alone. NKX6.1 was induced only weakly in all group 1 conditions, with the exception of RC (condition 5), which produced 45% PDX1/NKX6.1 double positive cells. NKX6.1 expression was also strongly induced when cells were exposed to retinoic acid alone or in combination with other factors followed by treatment with EK (group 2) or EKN (group 3) (FIGS. 2B and C, conditions 10-12 and 16-18). Endocrine differentiation, marked by NEUROG3 expression, was noted only when spheres had been exposed to N, either between days 5-9.5 (FIG. 2C, conditions 3, 6, 9, and 12) or starting at the end of day 8 (FIG. 2C, group 3, conditions 13-18). Very few NEUROG3+ cells were detected in all other conditions (FIG. 2C, conditions 1, 2, 4, 5, 7, 8, 10, and 11). qPCR analysis at day 8 of NEUROG3 and its downstream target NKX2.2 mRNA transcripts revealed significantly lower levels of these endocrine markers with R treatment when compared to the commonly employed RCN condition (FIG. 7D). Notably, addition of Vitamin C, recently shown to reduce endocrine differentiation in hESCs (Rezania et al, 2014), did not significantly lower NGN3 or NKX2.2 transcripts in our suspension culture system during RCN or R treatment (FIG. 7D). Taken together, these results indicate that R followed by EK treatment leads to highly efficient generation of PDX1+/NKX6.1+ progenitors (90%) and that the formation of bona fide NEUROG3 positive endocrine precursors is induced by treatment with N (FIG. 2 A-C, condition 10, green gates). Thus, by defining the temporal activities of individual signaling factors alone and in combination, we can induce transcription factor expression patterns characteristic of different human embryonic pancreatic progenitor cells types (PDX1+ and PDX1+/NKX6.1+ progenitors) without precocious induction of endocrine differentiation.

Example 4

Recapitulating Human Pancreas Organogenesis to Generate Endocrine Progenitors

Figure 3A:
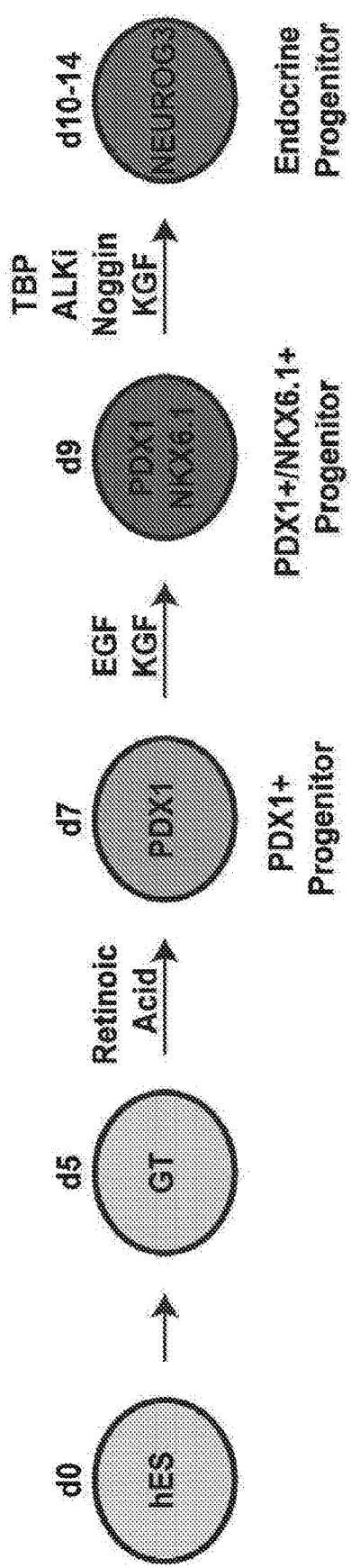
FIG. 3. Recapitulating human pancreas organogenesis to generate endocrine progenitors. A: Schematic outlining a simplified differentiation strategy for the controlled, step-wise generation of pancreatic progenitor cell types. B: Time-course flow cytometric analysis illustrates the efficient generation of PDX1+ progenitor (orange gate) and PDX1+/NKX6.1+ progenitor (blue gate) populations. Data from one of three independent experiments with similar results are shown. C: Immunofluorescence analysis of sections from differentiated clusters at indicated time points stained for human NKX2.2 (green) and NEUROG3 (red). Insets show NEUOG3/NKX2.2 double positive cells. Data from one of three independent experiments with similar results is shown.
Figure 3B:
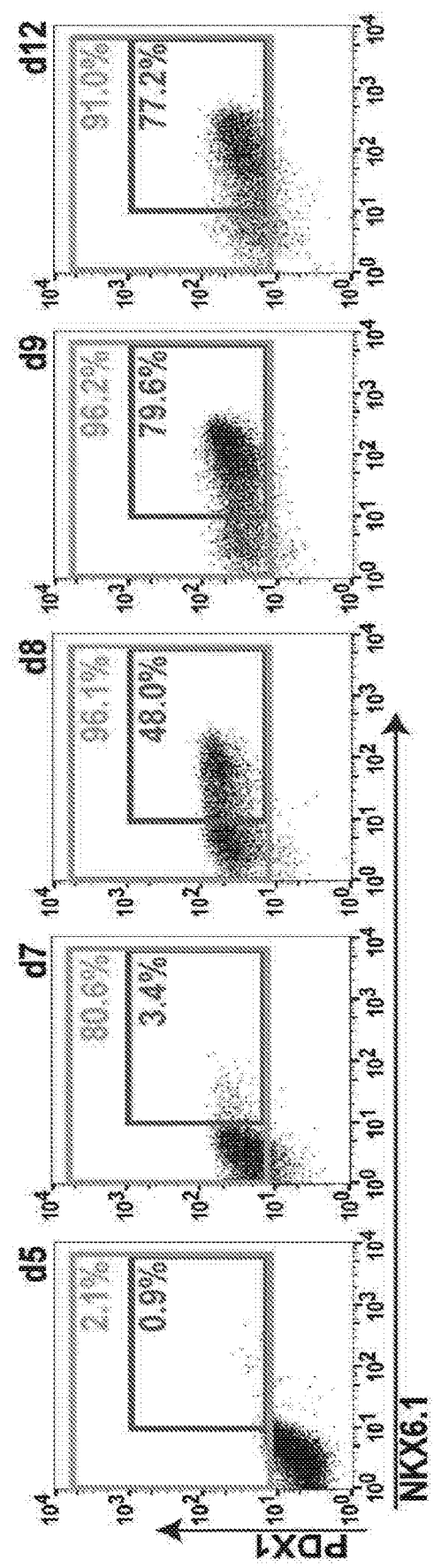
Figure 3C:
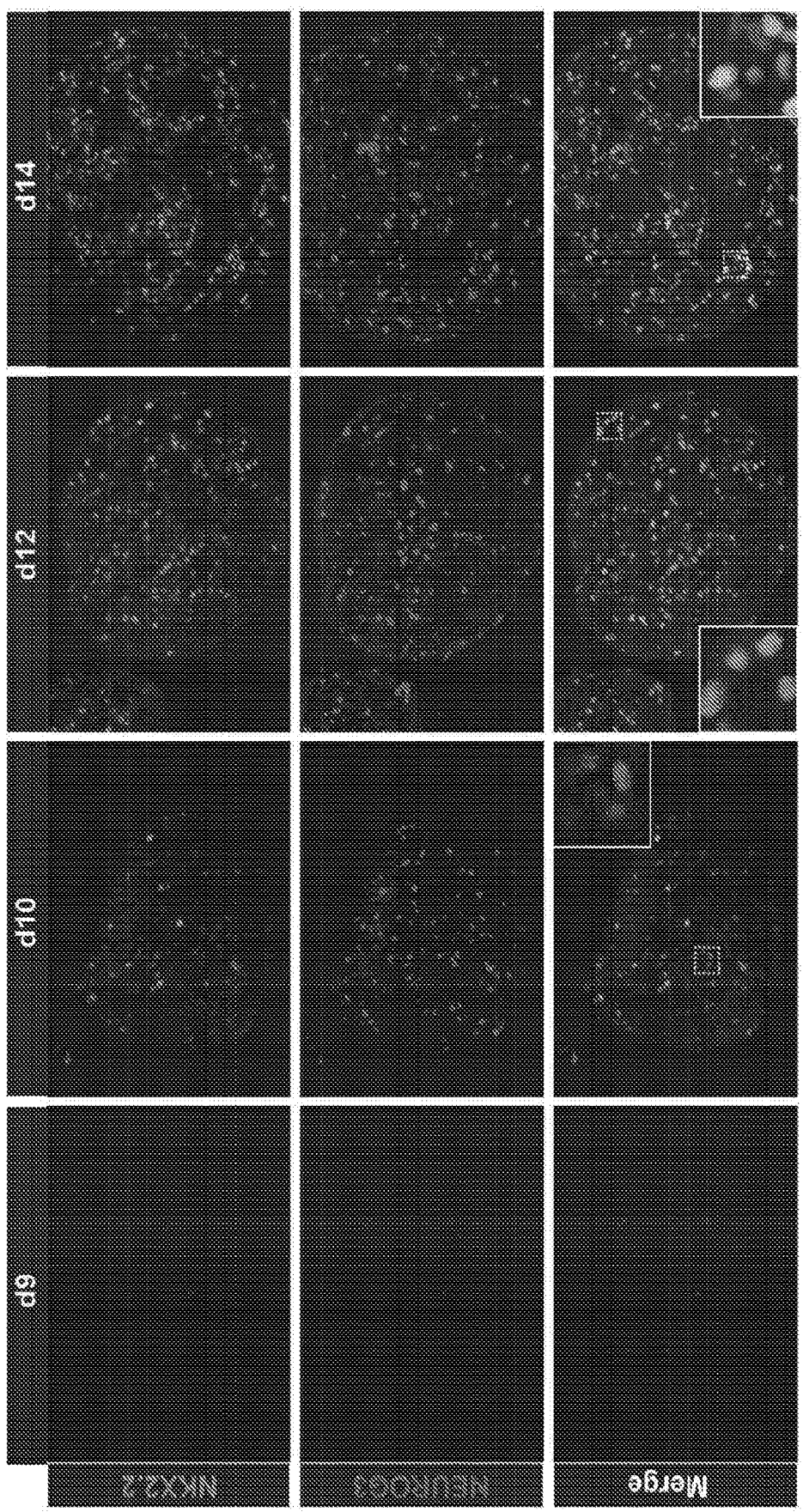

This improved and simplified differentiation protocol provides the basis for subsequent efficient formation of insulin-producing cells in suspension (FIG. 3A). Endocrine differentiation in PDX1/NKX6.1 double positive cells was induced by exposure to a cocktail of factors consisting of TBP (T), ALK inhibitor (A), N, and K, (TANK) which have previously been shown to activate NEUROG3 expression while maintaining high expression of PDX1 and NKX6.1 (Rezania et al, 2012; Nostro et al, 2011) (FIGS. 3A and B). While NEUROG3 protein was undetectable before TANK treatment (FIG. 3C, day 9), cells exhibiting nuclear accumulation of NEUROG3 protein appeared as early as one day following TANK treatment (FIG. 3C, day 10). Thus, expression of the pro-endocrine factor NEUROG3 is rapidly induced through TANK treatment once PDX1+/NKX6.1+ progenitors are specified (FIG. 3B, day 9). In contrast to the near-uniform generation of PDX1+ and PDX1+/NKX6.1+ progenitor populations following appropriate stimulation, endocrine differentiation appears to be confined to a smaller population of cells. This observation can be explained by the very short half-life of the NEUROG3 protein (Roark et al, 2012), which allows only transient detection of this marker in cells undergoing endocrine differentiation. NEUROG3+ cells, however, continued to be present when clusters were exposed to the endocrine differentiation cocktail for 5 days (FIG. 3C, day 14), indicating that endocrine cells were being generated throughout this period. To further characterize the progenitors present in our cultures at the initiation of endocrine differentiation, we analyzed the expression of NKX2.2, a downstream target of NEUROG3. NKX2.2 has recently been reported to have distinct expression patterns during pancreatic organogenesis in mouse and human (Jennings et al, 2013). While NKX2.2 is readily detectable in mouse pancreatic progenitor cells before NEUROG3 expression, NKX2.2 protein is only observed after endocrine commitment during human pancreas development. Similarly, we detected NKX2.2 protein expression only after endocrine differentiation is initiated at day 10, but not before in either PDX1+ or PDX1+/NKX6.1+ progenitors (FIG. 3C). Of note, some NKX2.2+ cells at day 10 co-express NEUROG3, and increasing numbers of NKX2.2+/NEUROG3-cells are found at later time points (FIG. 3C). These data indicate that NKX2.2 could serve as a lineage tracer for human cells that have undergone endocrine differentiation induced by transient NEUROG3 expression. In summary, we have established a novel differentiation strategy that faithfully recapitulates human pancreas organogenesis and allows for the precise control over the generation of PDX1+ and PDX1+/NKX6.1+ progenitors.

Example 5

Efficient Generation of PDX1+/NKX6.1+ Pancreatic Progenitor Cells Prior to Endocrine Induction Results in Glucose Responsive Beta-Like Cells.

Figure 4E:
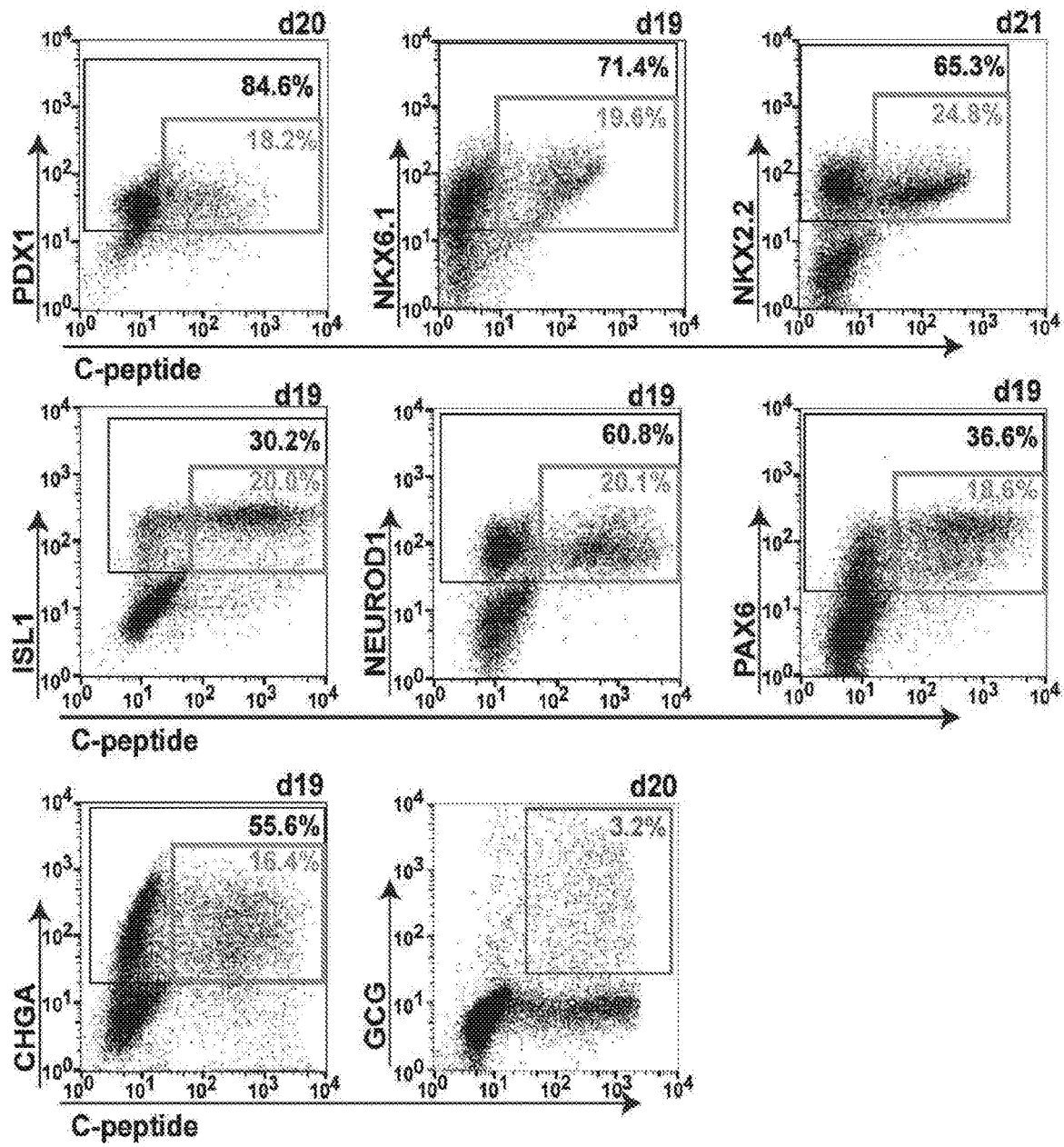
FIG. 4. Efficient generation of PDX1+/NKX6.1+ pancreatic progenitor cells prior to endocrine induction results in beta-like cells. A: Schematic outlining a simplified differentiation strategy for the controlled, step-wise generation of pancreatic progenitor and subsequent endocrine cell types. GFs=growth factors. B: Micrographs of differentiated clusters at day 19 under light microscopy (left picture) or fluorescent microscopy showing prominent GFP expression (right picture; GFP expression shown in white). C: Quantification of the percentage of human C-peptide positive cells at day 19-21. Values are average±SD. n=7 independent experiments. D: Immunofluorescence stainings of differentiated clusters at day 20 for insulin (INS), PDX1, NKX6.1, NKX2.2 and glucagon (GCG). One of four experiments with similar outcome is shown. E: Representative flow cytometry plots depicting co-expression of pancreatic markers PDX1, NKX6.1, NKX2.2, ISL1, NEUROD1, PAX6, ChromograninA (CHGA), and GCG with human C-peptide at indicated time points. Black gates mark percentage of total cells positive for indicated marker on 'Y' axis. Green gates mark percentage of double positive beta-like cells. The red gate marks percentage of INS+/GCG+ bihormonal cells. F: Flow cytometric quantification of C-peptide positive beta-like cells co-expressing markers in 'D'. A high percentage of beta-like cells co-express all genes usually found in beta cells, but not the hormone GCG. Values are average±SD. n=4 for PDX1, n=19 for NKX6.1, n=4 for NKX2.2, n=9 for ISL1, n=9 for NEUROD1, n=5 for PAX6, n=6 for CHGA, and n=5 for GCG. Analysis was performed at days 15-21 of differentiation.
Figure 4F:
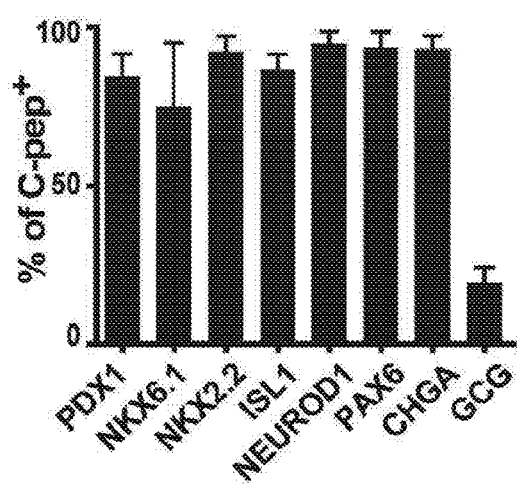
Figure 9A:
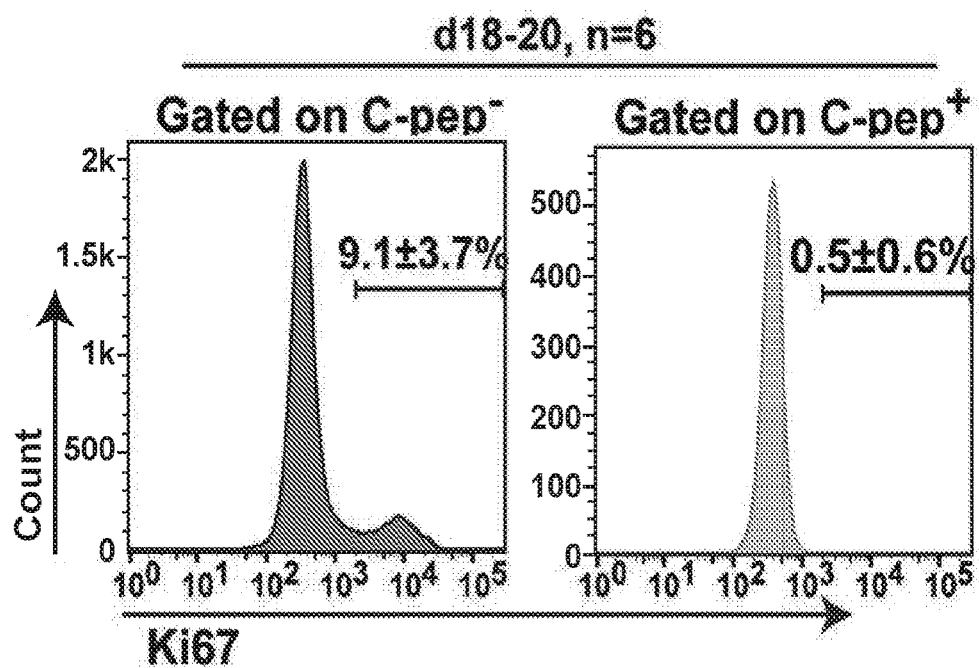
FIG. 9. hESC derived beta-like cells are post-mitotic. A: Proliferation of C-peptide+ beta-like cells and C-peptide negative cell populations at days 18-20 was determined by co-staining with the proliferation marker Ki67. B: Immunofluorescence staining of differentiated clusters at day 20 for the proliferation marker Ki67 and human insulin (INS). Representative data from one of three experiments with similar results are shown.
Figure 9B:
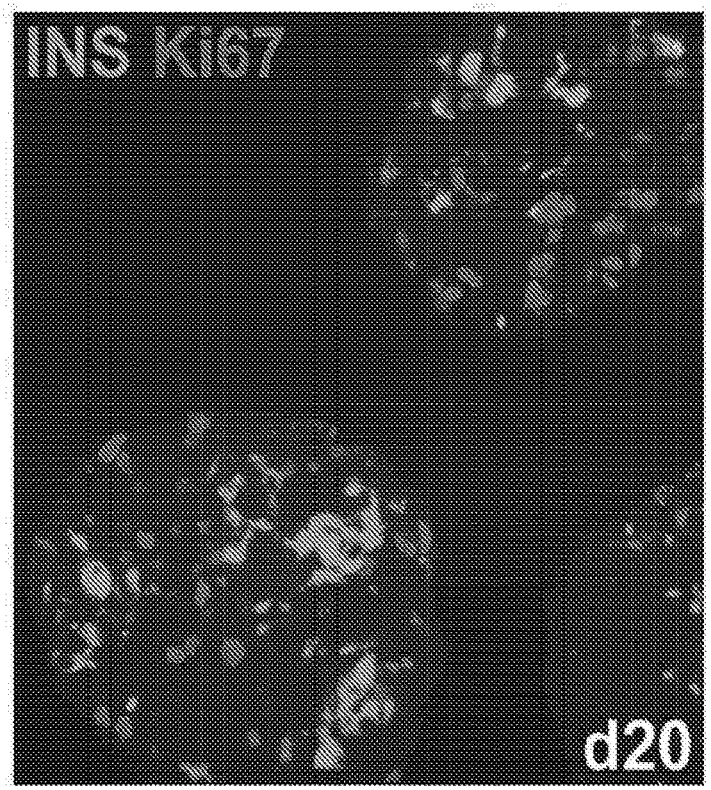

To test the expectation that precocious activation of NEUROG3 expression results in immature polyhormonal cells and not INS/NKX6.1 double positive beta-like cells, we initiated endocrine differentiation at day 7 in PDX1+ pancreatic progenitors by exposing the cells to NEUROG3 inducers ALKi and Noggin (FIG. 8A). While some single-hormone-positive cells were present at day 13, many endocrine cells were double-positive for C-peptide and glucagon (FIG. 8B). In further support of our expectation, virtually all C-peptide-positive cells lacked expression of NKX6.1 (FIG. 8C). To test whether correctly specified PDX1+/NKX6.1+ progenitor cells undergo differentiation towards INS/NKX6.1 double positive beta-like cells, we transferred spheres differentiated using our new method into a basal media without additional growth factors and monitored the establishment of beta-like cells (FIG. 4A). The percentage of GFP+ cells increased from day 13 to day 19, reaching an average of 23±6% human C-peptide-positive cells at days 19-21, likely reflecting continuous generation of insulin-producing cells for about 4 days after removal of NEUROG3-inducing factors (FIG. 4B, C). Immunofluorescence analysis of insulin-producing cells revealed co-expression and nuclear localization of TFs critical for beta cell function (PDX1, NKX6.1 and NKX2.2), but very few polyhormonal cells (FIG. 4D). Flow cytometry analysis of differentiated clusters showed a high percentage of total cells (black gates) and C-peptide positive beta-like cells (green gates) co-staining for PDX1, NKX6.1, NXK2.2, ISL1, PAX6, NeuroD1, and ChromograninA (CHGA) (FIG. 4E). These markers are normally found in both pancreatic progenitors and mature beta cells. Quantification of C-peptide+ beta-like cells co-staining for PDX1, NKX6.1, NKX2.2, ISL1, NEUROD1, PAX6 and Chromogranin A showed 84±7%, 75±20%, 92±5%, 86±5%, 95±4%, 93±5%, and 93±4% double positive cells, respectively (FIG. 4F). Notably, only 3.2% of all differentiated cells co-expressed C-peptide and the hormone glucagon (FIG. 4E, red gate). An important hallmark of mature human beta cells is their restricted proliferative capacity. While 9.1±3.7% of C-peptide-negative cells were actively proliferating, only 0.5±0.6% of C-peptide-positive beta-like cells co-stain for the proliferation marker Ki67, indicating their terminal differentiation state (FIGS. 9A and B). Thus, our optimized differentiation strategy results in the predominant generation of post-mitotic, insulin-producing beta-like cells that co-express critical beta cell markers.

Figure 5:
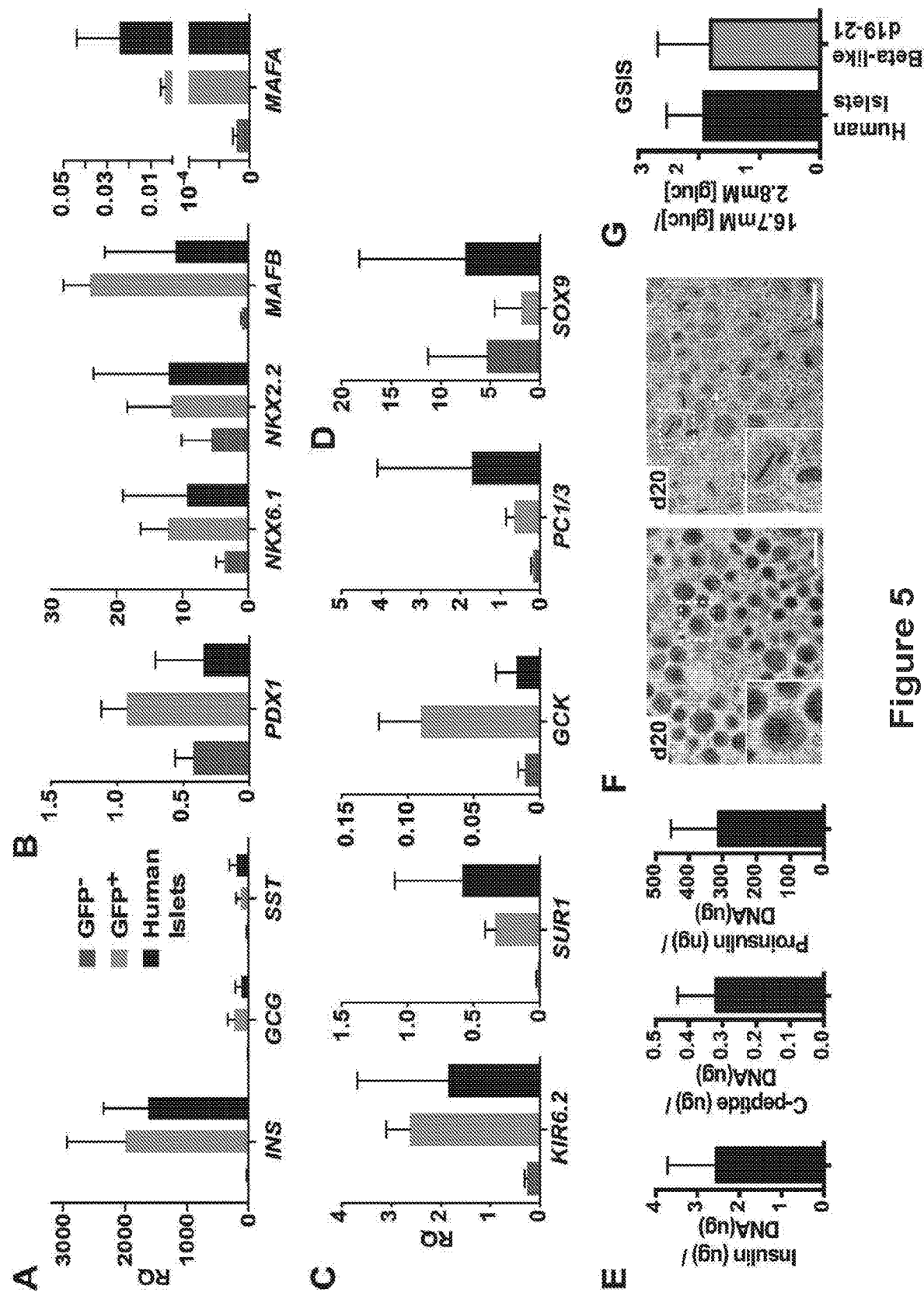
FIG. 5. Beta-like cells exhibit key features of bona fide human beta cells and are glucose responsive. A-D: Quantitative PCR analysis of selected gene transcripts in sorted GFP+ beta-like cells (green bars), GFP-populations (blue bars) and human islet preparations (black bars). Results shown relative to the endogenous control GAPDH. RQ=relative quantification. Values are average±SD. n=4 independent experiments for hESC-derived cell populations at days 19-20 and n=3 for human islets. E: Insulin, human C-peptide, and proinsulin content relative to DNA in beta-like cells at day 19. Data presented is average±standard error (n=3 independent experiments, technical duplicates). F: Transmission electron microscopy images of beta-like cells at day 20. One of three experiments with similar results is shown. Scale bar=500 nm. Insets represent secretory vesicles akin to granules present in bona fide human beta cells. G: Glucose-stimulated insulin secretion (GSIS) of human islets and beta-like cells at days 19-20. "Y" axis indicates ratio of insulin secreted in low glucose conditions to that secreted in high glucose conditions. Values are average±standard deviation (SD) (n=3 for human islets and n=10 for beta-like cells).
Figure 7A:
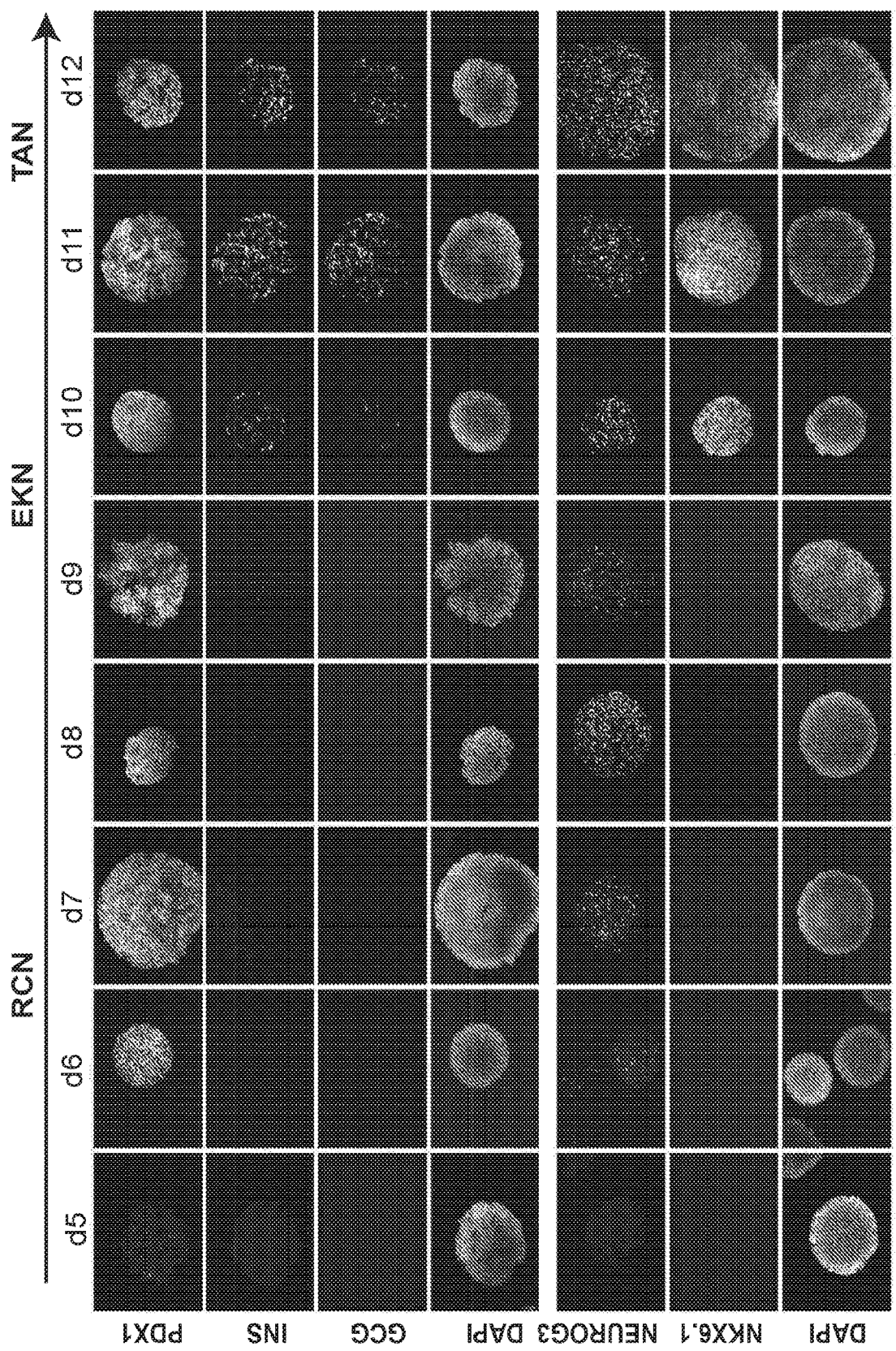
FIG. 7. Published protocols result in precocious endocrine differentiation by NEUROG3 activation. A-C: Analysis of key pancreatic progenitor markers in clusters differentiated as outlined in FIG. 1A. R=Retinoic acid, C=Cyclopamine, N=Noggin, E=Epidermal growth factor, K=Keratinocyte growth factor, T=TBP, and A=ALK inhibitor. Data shown are representative of two independent experiments. A: PDX1, INS, GCG, NEUROG3, and NKX6.1 protein expression was assessed by whole mount staining of differentiated clusters at indicated time points. Note precocious expression of the endocrine marker NEUROG3 in the absence of NKX6.1 protein at days 6-9. B and C: Flow cytometric quantification of PDX1+(orange gate), PDX1+/NKX6.1+ (blue gate), INS+/NKX6.1+ (green gate), and INS+/NKX6.1− (red gate) cells at indicated time points. D: qPCR analysis of NGN3 and NKX2.2 transcripts at day 8 of differentiation employing RCN (Retinoic acid (R), Cyclopamine (C), and Noggin (N)) or R with two different concentrations of Vitamin C (Vit. C) treatment for 3 days or without treatment. Data are shown as the average±standard error, relative to RCN and normalized to GAPDH. (n=three independent experiments, technical duplicates).
Figure 7B:
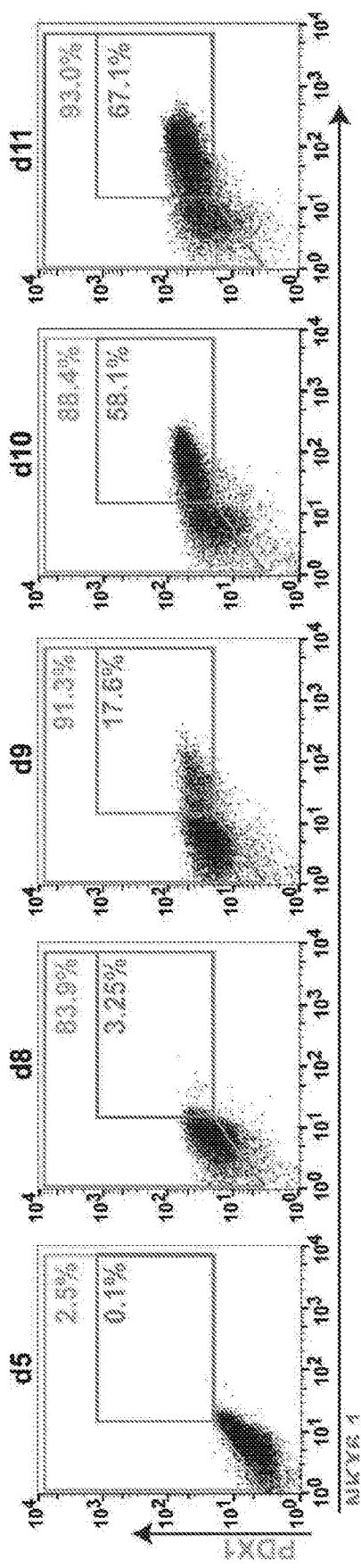
Figure 7C:
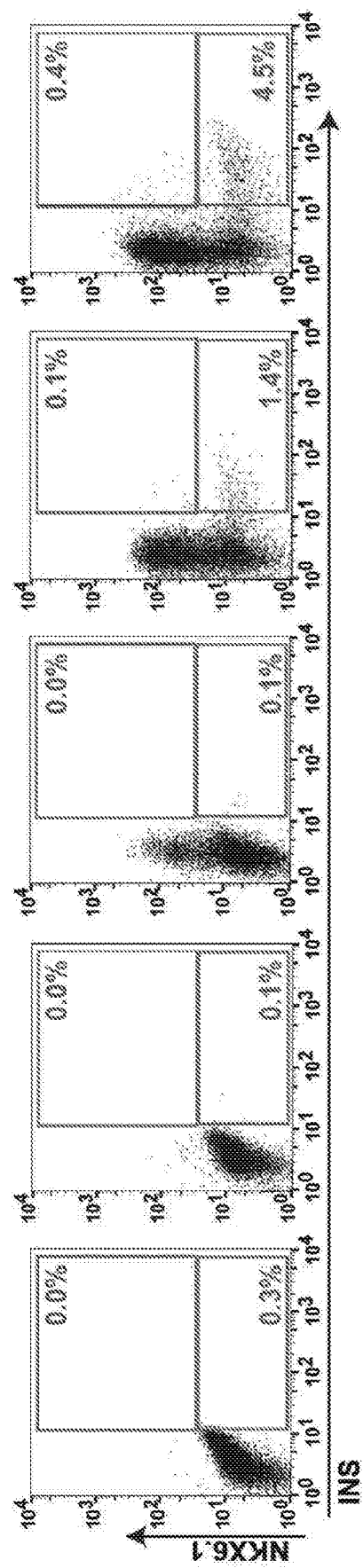
Figure 7D:
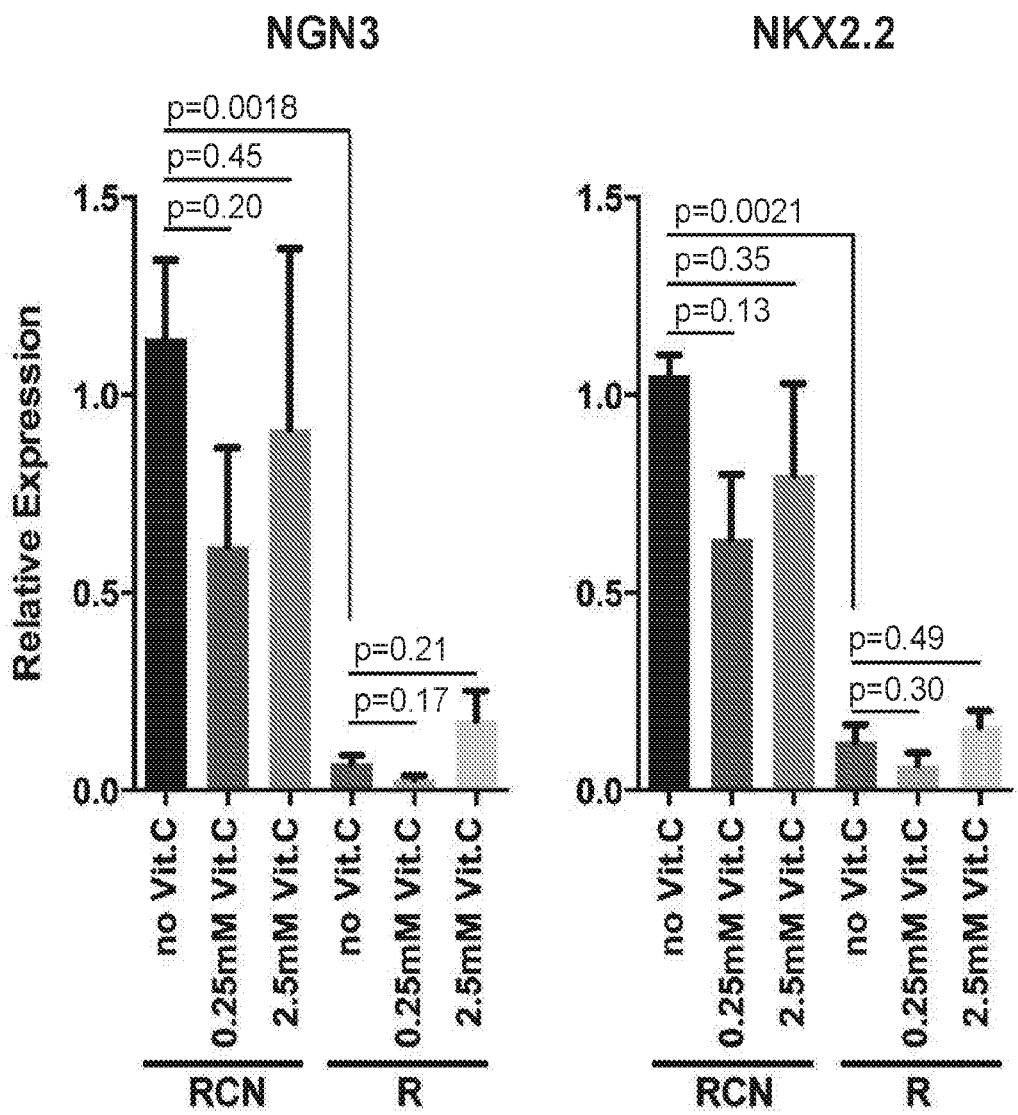
Figure 10A:
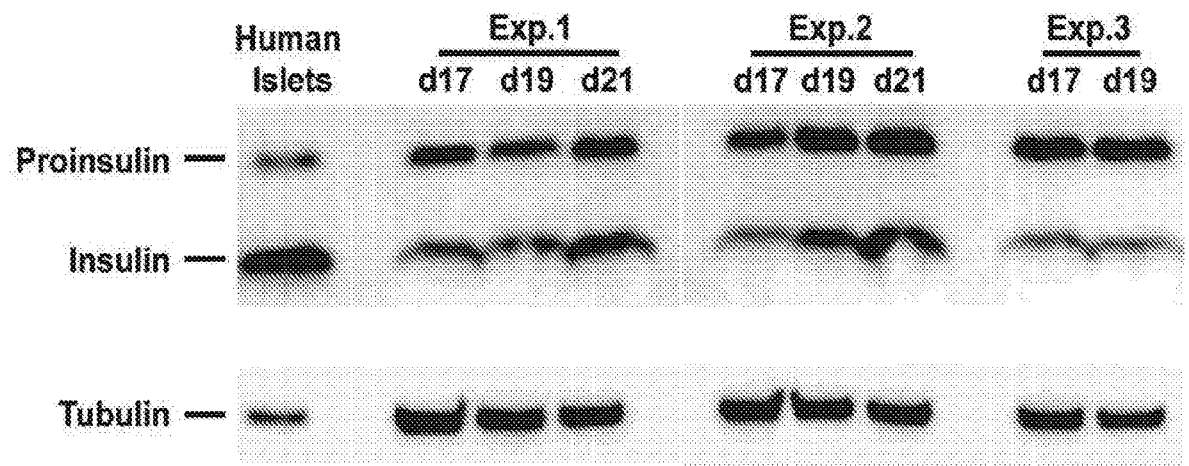
FIG. 10. Efficient processing of insulin in hESC derived beta-like cells. A: Western blot analysis of proinsulin processing to insulin in beta-like cells at indicated time points. A human islet preparation is shown for comparison. Proceeding from left to right, Western blot panels of the following are provided: i) two human islet preparations, ii) hES9.3 cells sampled at days 17, 19 and 21, iii) hES9.6 cells sampled at days 17, 19 and 21, and iv) hES9.10 cells sampled at days 17 and 19, are shown The Western blot was cropped to conserve space, enabling tubulin levels to be shown (as a higher molecular weight protein, tubulin ran above proinsulin and insulin in the gel subjected to Western blot). B: Quantification of proinsulin processing in FIG. 5E and panel A. n=3 for each time point of beta-like cells and n=4 for human islets.
Figure 10B:
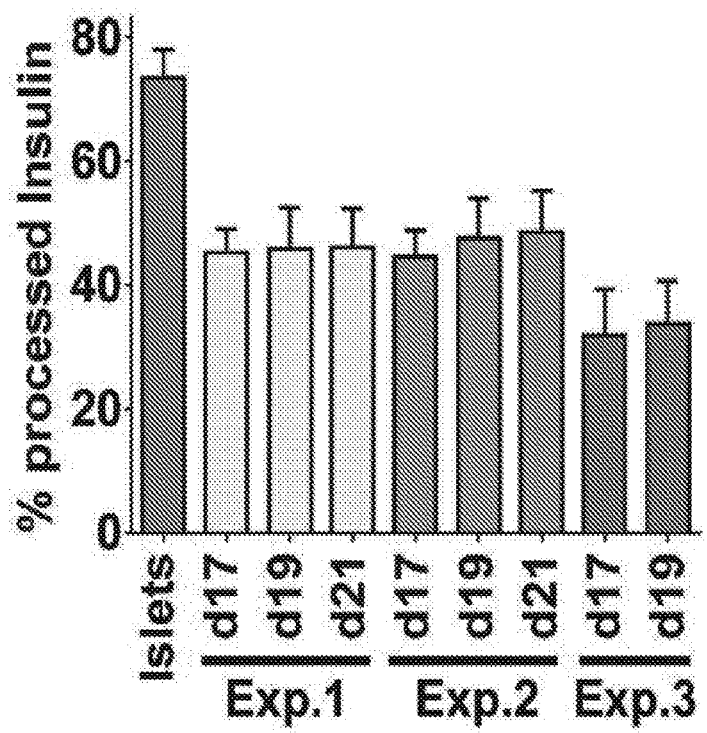

To further characterize gene expression in beta-like cells at days 19-20, we took advantage of the GFP live marker to compare sorted GFP+ beta-like cells and GFP-populations to purified human islets. hESC-derived beta-like cells showed high levels of insulin gene transcripts, comparable to cadaveric islet preparations, while GFP-negative populations exhibit only insignificant levels of the hormone (FIG. 5A). We also detected transcript levels for two other hormones (GCG and SST) in GFP+ cells, likely due to contamination by the small number of polyhormonal cells also expressing the GFP reporter (FIGS. 5A and 4D and E). Consistent with the immunofluorescence analysis (FIG. 4D), transcripts for the TFs PDX1, NKX6.1 and NKX2.2 normally found in both progenitor and mature beta cells were expressed at comparable levels in GFP-negative, GFP-positive, and islet cells (FIG. 5B). Transcripts for the mature human beta cell transcription factors MAFA and MAFB were robustly expressed in human islets and enriched in beta-like cells compared to GFP-populations. MAFB transcript levels in beta-like cells were similar to human islets; MAFA expression levels were slightly lower (FIG. 5B). Other genes important for human beta cell functionality, including the KATP channel components Potassium Inwardly-Rectifying Channel, Subfamily J, Member 11 (KIR6.2 also known as KCJN11) and ATP-Binding Cassette, Sub-Family C, Member 8 (SUR1 also known as ABCC8), the glucose metabolism enzyme Glucokinase (GCK, also known as HK4), and the Prohormone Convertase ⅓ (PC⅓) necessary for insulin biosynthesis, were enriched in GFP-positive beta-like cells at levels similar to or exceeding those found in human islets (FIG. 5C). In contrast, mRNA levels for the progenitor marker SOX9 were reduced in beta-like cells compared to GFP-progenitors (FIG. 5D). The somewhat higher SOX9 expression in human islets is likely the result of contamination with Sox9-positive duct cells. Thus, our gene expression analysis indicated that hESC-derived beta-like cells possess the molecular machinery necessary for beta cell function, including insulin biosynthesis and glucose metabolism. Further investigations revealed that day 19 beta-like cells contain 2.5±1.2 ug, 0.32±0.12 ug, and 310±143 ng insulin, human c-peptide, and proinsulin per μg DNA, respectively (FIG. 5E). These values are comparable to about 2.8 ug insulin, about 0.55 ug c-peptide, and about 150 ng proinsulin per μg DNA for human islets, as recently published (Rezania et al, 2014). Western blot analysis for proinsulin and mature insulin further confirmed efficient insulin protein processing in hESC-derived beta-like cells, reaching 59±2% of the extent of processing observed in purified human islets (FIGS. 10A and B). Ultrastructural analysis of differentiated cell clusters by transmission electron microscopy revealed that many cells contained secretory vesicles exhibiting electron dense cores or rod-like structures, akin to what is observed in human beta cells (FIG. 5F). To further investigate the functional properties of in vitro differentiated beta-like cells, we performed glucose stimulated insulin secretion assays, in which we measured the release of human C-peptide, a by-product of endogenous insulin biosynthesis secreted in an equimolar ratio to insulin. hESC-derived beta-like cells analyzed at days 19-21 responded to an increase in glucose concentration from 2.8 mM to 16.7 mM by secreting 1.8±0.9-fold more C-peptide, a response similar to the 1.9±0.6-fold increase detected with human islets (FIG. 5G). Thus, beta-like cells generated by our optimized differentiation strategy express critical beta cell genes, synthesize high levels of mature insulin, exhibit ultrastructural features of bona fide beta cells and secrete endogenous insulin in response to changes in physiological concentrations of glucose.

Example 6 hESC-Derived Beta-Like Cells Remain Glucose Responsive after Short Term Transplantation.

To determine whether hESC-derived beta-like cells can maintain their glucose responsiveness in vivo, we transplanted approximately 5 million cells under the kidney capsule of immunodeficient mice (days 19-21 spheres consisting of progenitors and beta-like cells). Mice transplanted with 4000 human islets served as controls. Seven to 10 days post-surgery, human C-peptide levels were measured in overnight-fasted mice, before and after the administration of a glucose bolus. As expected, mice that received human islet grafts exhibited low levels of insulin secretion upon fasting, followed by a marked increase in circulating insulin after glucose challenge (average of 221±116 pM, FIG. 6A). Similar to mice carrying human islets, fasted mice transplanted with hESC-derived beta-like cells had low levels of circulating C-peptide. Upon glucose administration, C-peptide concentrations in sera of these mice also increased, albeit at lower levels than in mice transplanted with human islets (average of 40±28 pM, FIG. 6A). This lower number might be explained in part by the different numbers of cells transplanted in the human islet and beta-like cell groups. Indeed, each human islet contains on average 1000 cells, of which 50% are beta cells (Cabrera et al, 2006). Thus, 4000 human islets contain approximately $2.0 \times 10^6$ bona fide beta cells. Because hESC differentiated spheres contain on average 23% beta-like cells, only about $1.15 \times 10^6$ beta-like cells were transplanted per mouse. Normalization based on beta cell number indicates that hESC derived beta-like cells secreted 70±48 pM human c-peptide per $2.0 \times 10^6$ cells, representing approximately ⅓ of the insulin secreted from each human cadaveric beta cell (FIG. 6A). Hematoxylin and Eosin staining, together with immunofluorescence analysis of the hESC grafts at 2 weeks post-transplantation demonstrated prominent islet-like structures positive for human C-peptide (FIGS. 6B and C). Beta-like cells also maintained co-expression of the key beta cell TFs PDX1, NKX6.1 and NKX2.2, and only a few cells co-expressed other hormones, such as glucagon and somatostatin (FIG. 6C). To further investigate the functional properties of hES derived beta-like cells in vivo, we transplanted clusters under the kidney capsule of mice rendered diabetic through treatment with the beta cell toxin streptozotocin. Mice that received grafts exhibit significantly reduced blood glucose (BG) levels at all time points analyzed when compared to control animals (FIG. 6D). While BG levels were significantly reduced in graft-bearing mice, they continued to exhibit hyperglycemic BG values over time. This is likely due to the limited number of beta-like cells that can be transplanted under the kidney capsule in one mouse. It has previously been shown that 4,000 human islets are required to establish long-term euglycemia in diabetic mice. Transplantation of a smaller number of human islets (1,500 islets) reduces blood glucose levels only for 7 days post-transplantation, after which hyperglycemia returned (Fiaschi-Taesch et al, 2010). Our surgical procedure permits the transplantation of about $1.15 \times 10^6$ beta-like cells, substantially less than the approximately $2.0 \times 10^6$ beta cells present in the 4,000 human islets previously found to be required for the long-term reversal of diabetes. Hence, the observed reduction in BG levels, but lack of complete diabetes reversal in mice bearing hES-derived transplants, is not unexpected given this technical constraint. Taken together, the in vivo data demonstrate that hESC derived beta-like cells maintain their differentiated phenotype and remain glucose responsive after a short engraftment period in vivo and highlights their potential therapeutic value.

Each of the references listed below and cited throughout the disclosure is incorporated by reference herein in its entirety, or in relevant part, as would be apparent from context.

REFERENCES

Barton F B, Rickels M R, Alejandro R, Hering B J, Wease S, Naziruddin B, Oberholzer J, Odorico J S, Garfinkel M R, Levy M, Pattou F, Berney T, Secchi A, Messinger S, Senior P A, Maffi P, Posselt A, Stock P G, Kaufman D B, Luo X, et al (2012) Improvement in outcomes of clinical islet transplantation: 1999-2010. Diabetes Care 35: 1436-1445.

Bouwens L, Houbracken I & Mfopou J K (2013) The use of stem cells for pancreatic regeneration in diabetes mellitus. Nat Rev Endocrinol 9: 598-606.

Cabrera O, Berman D M, Kenyon N S, Ricordi C, Berggren P-O & Caicedo A (2006) The unique cytoarchitecture of human pancreatic islets has implications for islet cell function. Proc. Natl. Acad. Sci. U.S.A. 103: 2334-2339.

Chen S, Borowiak M, Fox J L, Maehr R, Osafune K, Davidow L, Lam K, Peng L F, Schreiber S L, Rubin L L & Melton D (2009) A small molecule that directs differentiation of human ESCs into the pancreatic lineage. Nat. Chem. Biol. 5:258-265.

D'Amour K A, Agulnick A D, Eliazer S, Kelly O G, Kroon E & Baetge E E (2005) Efficient differentiation of human embryonic stem cells to definitive endoderm. Nat. Biotechnol. 23: 1534-1541.

D'Amour K A, Bang A G, Eliazer S, Kelly O G, Agulnick A D, Smart N G, Moorman M A, Kroon E, Carpenter M K & Baetge E E (2006) Production of pancreatic hormone-expressing endocrine cells from human embryonic stem cells. Nat. Biotechnol. 24: 1392-1401.

De Krijger R R, Aanstoot H J, Kranenburg G, Reinhard M, Visser W J & Bruining G J (1992) The midgestational human fetal pancreas contains cells coexpressing islet hormones. Developmental Biology 153: 368-375.

Efrat S & Russ H A (2012) Making 13 cells from adult tissues. Trends in Endocrinology & Metabolism 23: 278-285.

Fiaschi-Taesch N M, Salim F, Kleinberger J, Troxell R, Cozar-Castellano I, Selk K, Cherok E, Takane K K, Scott D K & Stewart A F (2010) Induction of Human-Cell Proliferation and Engraftment Using a Single G1/S Regulatory Molecule, cdk6. Diabetes 59: 1926-1936.

Gu G, Dubauskaite J & Melton D A (2002) Direct evidence for the pancreatic lineage: NGN3+ cells are islet progenitors and are distinct from duct progenitors. Development 129: 2447-2457.

Guo S, Dai C, Guo M, Taylor B, Harmon J S, Sander M, Robertson R P, Powers A C & Stein R (2013a) Inactivation of specific 13 cell transcription factors in type 2 diabetes. J. Clin. Invest. 123: 3305-3316.

Guo T, Landsman L, Li N & Hebrok M (2013b) Factors Expressed by Murine Embryonic Pancreatic Mesenchyme Enhance Generation of Insulin-Producing Cells From hESCs. Diabetes.

Haataja L, Snapp E, Wright J, Liu M, Hardy A B, Wheeler M B, Markwardt M L, Rizzo M & Aryan P (2013) Proinsulin intermolecular interactions during secretory trafficking in pancreatic ß cells. Journal of Biological Chemistry 288:1896-1906.

Hebrok M (2003) Hedgehog signaling in pancreas development. Mech. Dev. 120:45-57.

Hebrok M (2012) Generating β cells from stem cells—the story so far. Cold Spring Harb Perspect Med 2: a007674.

Herrera P L, Népote V & Delacour A (2002) Pancreatic cell lineage analyses in mice. Endocrine 19: 267-278.

Hua H, Shang L, Martinez H, Freeby M, Gallagher M P, Ludwig T, Deng L, Greenberg E, Leduc C, Chung W K, Goland R, Leibel R L & Egli D (2013) iPSC-derived 13 cells model diabetes due to glucokinase deficiency. J. Clin. Invest.

Jennings R E, Berry A A, Kirkwood-Wilson R, Roberts N A, Hearn T, Salisbury R J, Blaylock J, Piper Hanley K & Hanley N A (2013) Development of the human pancreas from foregut to endocrine commitment. Diabetes 62: 3514-3522.

Johansson K A, Dursun U, Jordan N, Gu G, Beermann F, Gradwohl G & Grapin-Botton A (2007) Temporal control of neurogenin3 activity in pancreas progenitors reveals competence windows for the generation of different endocrine cell types. Developmental Cell 12: 457-465.

Kelly O G, Chan M Y, Martinson L A, Kadoya K, Ostertag T M, Ross K G, Richardson M, Carpenter M K, D'Amour K A, Kroon E, Moorman M, Baetge E E & Bang A G (2011) Cell-surface markers for the isolation of pancreatic cell types derived from human embryonic stem cells. Nat. Biotechnol. 29: 750-756.

Kroon E, Martinson L A, Kadoya K, Bang A G, Kelly O G, Eliazer S, Young H, Richardson M, Smart N G, Cunningham J, Agulnick A D, D'Amour K A, Carpenter M K & Baetge E E (2008) Pancreatic endoderm derived from human embryonic stem cells generates glucose-responsive insulin-secreting cells in vivo. Nat. Biotechnol. 26: 443-452.

Liu H, Yang H, Zhu D, Sui X, Li J, Liang Z, Xu L, Chen Z, Yao A, Zhang L, Zhang X, Yi X, Liu M, Xu S, Zhang W, Lin H, Xie L, Lou J, Zhang Y, Xi J, et al (2014) Systematically labeling developmental stage-specific genes for the study of pancreatic. Cell Res.: 1-20.

Maehr R, Chen S, Snitow M, Ludwig T, Yagasaki L, Goland R, Leibel R L & Melton D A (2009) Generation of pluripotent stem cells from patients with type 1 diabetes. Proc. Natl. Acad. Sci. U.S.A. 106: 15768-15773.

Mfopou J K, Chen B, Mateizel I, Sermon K & Bouwens L (2010) Noggin, retinoids, and fibroblast growth factor regulate hepatic or pancreatic fate of human embryonic stem cells. Gastroenterology 138: 2233-45, 2245.e1-14.

Micallef S J, Li X, Schiesser J V, Hirst C E, Yu Q C, Lim S M, Nostro M C, Elliott D A, Sarangi F, Harrison L C, Keller G, Elefanty A G & Stanley E G (2012) INS (GFP/w) human embryonic stem cells facilitate isolation of in vitro derived insulin-producing cells. Diabetologia 55: 694-706.

Murtaugh L C & Melton D A (2003) Genes, signals, and lineages in pancreas development. Annu. Rev. Cell Dev. Biol. 19: 71-89.

Nostro M-C & Keller G (2012) Generation of beta cells from human pluripotent stem cells: Potential for regenerative medicine. Seminars in Cell and Developmental Biology 23: 701-710.

Nostro M C, Sarangi F, Ogawa S, Holtzinger A, Corneo B, Li X, Micallef S J, Park I-H, Basford C, Wheeler M B, Daley G Q, Elefanty A G, Stanley E G & Keller G (2011) Stage-specific signaling through TGFß family members and WNT regulates patterning and pancreatic specification of human pluripotent stem cells. Development 138: 861-871.

Pagliuca F W & Melton D A (2013) How to make a functional β-cell. Development 140: 2472-2483.

Pagliuca F W, Millman J R, Giirtler M, Segel M, Van Dervort A, Ryu J H, Peterson Q P, Greiner D & Melton D A (2014) Generation of Functional Human Pancreatic b Cells In Vitro. Cell 159: 428-439.

Pan F C & Wright C (2011) Pancreas organogenesis: from bud to plexus to gland. Dev. Dyn. 240: 530-565.

Posselt A M, Szot G L, Frassetto L A, Masharani U, Tavakol M, Amin R, McElroy J, Ramos M D, Kerlan R K, Fong L, Vincenti F, Bluestone J A & Stock P G (2010) Islet Transplantation in Type 1 Diabetic Patients Using Calcineurin Inhibitor-Free Immunosuppressive Protocols Based on T-Cell Adhesion or Costimulation Blockade. Transplantation 90: 1595-1601.

Rezania A, Bruin J E, Arora P, Rubin A, Batushansky I, Asadi A, O'Dwyer S, Quiskamp N, Mojibian M, Albrecht T, Yang Y H C, Johnson J D & Kieffer T J (2014) Reversal of diabetes with insulin-producing cells derived in vitro from human pluripotent stem cells. Nat. Biotechnol.

Rezania A, Bruin J E, Riedel M J, Mojibian M, Asadi A, Xu J, Gauvin R, Narayan K, Karanu F, O'Neil J J, Ao Z, Warnock G L & Kieffer T J (2012) Maturation of Human Embryonic Stem Cell-Derived Pancreatic Progenitors Into Functional Islets Capable of Treating Pre-existing Diabetes in Mice. Diabetes 61: 2016-2029.

Rezania A, Riedel M J, Wideman R D, Karanu F, Ao Z, Warnock G L & Kieffer T J (2011) Production of functional glucagon-secreting a-cells from human embryonic stem cells. Diabetes 60: 239-247.

Riedel M J, Asadi A, Wang R, Ao Z, Warnock G L & Kieffer T J (2011) Immunohistochemical characterisation of cells co-producing insulin and glucagon in the developing human pancreas. Diabetologia 55: 372-381.

Roark R, Itzhaki L & Philpott A (2012) Complex regulation controls Neurogenin3 proteolysis. Biol Open 1: 1264-1272.

Russ H A & Efrat S (2011) In-Vivo Functional Assessment of Engineered Human Insulin-Producing Cells (Artech House).

Schaffer A E, Freude K K, Nelson S B & Sander M (2010) Nkx6 Transcription Factors and Ptf1a Function as Antagonistic Lineage Determinants in Multipotent Pancreatic Progenitors. Developmental Cell 18: 1022-1029.

Schulz T C, Young H Y, Agulnick A D, Babin M J, Baetge E E, Bang A G, Bhoumik A, Cepa I, Cesario R M, Haakmeester C, Kadoya K, Kelly J R, Kerr J, Martinson L A, McLean A B, Moorman M A, Payne J K, Richardson M, Ross K G, Sherrer E S, et al (2012) A scalable system for production of functional pancreatic progenitors from human embryonic stem cells. PLoS ONE 7: e37004.

Seymour P A & Sander M (2011) Historical Perspective: Beginnings of the-Cell: Current Perspectives in-Cell Development. Diabetes 60: 364-376.

Shang L, Hua H, Foo K, Martinez H, Watanabe K, Zimmer M, Kahler D J, Freeby M, Chung W, Leduc C, Goland R, Leibel R L & Egli D (2014) ß-cell dysfunction due to increased E R stress in a stem cell model of Wolfram syndrome. Diabetes 63: 923-933.

Shapiro A M, Lakey J R, Ryan E A, Korbutt G S, Toth E, Warnock G L, Kneteman N M & Rajotte R V (2000) Islet transplantation in seven patients with type 1 diabetes mellitus using a glucocorticoid-free immunosuppressive regimen. N. Engl. J. Med. 343: 230-238.

Shih H P, Kopp J L, Sandhu M, Dubois C L, Seymour P A, Grapin-Botton A & Sander M (2012) A Notch-dependent molecular circuitry initiates pancreatic endocrine and ductal cell differentiation. Development 139: 2488-2499.

Shim J-H, Kim J, Han J, An S Y, Jang Y J, Son J, Woo D-H, Kim S-K & Kim J-H (2014) Pancreatic islet-like three dimensional aggregates derived from human embryonic stem cells ameliorate hyperglycemia in streptozotocin induced diabetic mice. cell transplant.

Szot G L, Koudria P & Bluestone J A (2007) Transplantation of Pancreatic Islets Into the Kidney Capsule of Diabetic Mice. J Vis Exp.

Szot G L, Yadav M, Lang J, Kroon E, Kerr J, Kadoya K, Brandon E P, Baetge E E, Bour-Jordan H & Bluestone J A (2014) Tolerance Induction and Reversal of Diabetes in Mice Transplanted with Human Embryonic-Stem-Cell-Derived Pancreatic Endoderm. Cell Stem Cell.

Tudurf E & Kieffer T J (2011) Reprogramming gut and pancreas endocrine cells to treat diabetes. Diabetes, Obesity and Metabolism 13 Suppl 1: 53-59.

Van Hoof D, Mendelsohn A D, Seerke R, Desai T A & German M S (2011) Differentiation of human embryonic stem cells into pancreatic endoderm in patterned size-controlled clusters. Stem Cell Res 6: 276-285.

Xu X, Browning V & Odorico J S (2011) Activin, BMP and FGF pathways cooperate to promote endoderm and pancreatic lineage cell differentiation from human embryonic stem cells. Mech. Dev.

Zhou Q & Melton D A (2008) Extreme makeover: converting one cell into another. Cell Stem Cell 3: 382-388.

The disclosed subject matter has been described with reference to various specific embodiments and techniques. It should be understood, however, that many variations and modifications may be made while remaining within the spirit and scope of the disclosed subject matter.

What is claimed is:

1. A method of generating a PDX1+/NKX6.1+ progenitor cell comprising contacting an embryonic stem cell with an effective amount of a retinoic acid compound to induce a PDX1+ progenitor cell, further comprising contacting the PDX1+ progenitor cell with effective amounts of epidermal growth factor and keratinocyte growth factor, wherein the PDX1+ progenitor cell is not contacted with a bone morphogenic protein (BMP) inhibitor prior to expression of NKX6.1 by the cell, thereby inducing formation of a PDX1+/NKX6.1+ progenitor cell.

2. The method according to claim 1 wherein the embryonic stem cell is a human embryonic stem cell.

3. The method according to claim 1 wherein the embryonic stem cell is contacted with a retinoic acid compound in vitro.

4. The method according to claim 1 further comprising inducing the PDX1+/NKX6.1+ progenitor cell to express NEUROG3, wherein the NEUROG3 expression is induced by contacting the PDX1+/NKX6.1+ progenitor cell with an effective amount of an inhibitor of bone morphogenetic protein, an inhibitor of TGFβ/ALK, or an inhibitor of sonic hedgehog, resulting in production of an INS+/NKX6.1+ cell.

5. The method according to claim 4 wherein the PDX1+/NKX6.1+ progenitor cell is contacted by an effective amount of the inhibitor of bone morphogenetic protein and an effective amount of an inhibitor of TGFβ/ALK.

6. The method according to claim 5 wherein the PDX1+/NKX6.1+ progenitor cell is contacted by an effective amount of an inhibitor of bone morphogenetic protein and an effective amount of an inhibitor of sonic hedgehog.

7. The method according to claim 4 wherein the inhibitor of bone morphogenetic protein is Noggin or the inhibitor of sonic hedgehog is Cyclopamine.

8. The method according to claim 4 wherein the NEUROG3 expression is induced by exposure of the PDX1+/NKX6.1+ progenitor cell to effective amounts of a TATA-Binding Protein, an Activin receptor-Like Kinase inhibitor, Noggin and Keratinocyte Growth Factor.

9. The method according to claim 4 wherein the NEUROG3 expression begins before expression of NKX2.2 is detected.

10. The method according to claim 1 wherein no more than 5% of the PDX1+ progenitor cells are polyhormonal cells.

11. The method according to claim 4 wherein the INS+/NKX6.1+ cell is a beta-like cell responsive to glucose levels.

12. The method according to claim 11 wherein the INS+/NKX6.1+ beta-like cell secretes an increased level of insulin in response to an increased glucose level.

13. The method according to claim 4 wherein the INS+/NKX6.1+ cell does not express a detectable level of a Ki67 marker.

14. A method of using the INS+/NKX6.1+ cell according to claim 8 compromising transplanting the INS+/NKX6.1+ cell into a human.

15. The method according to claim 14 wherein the human is diabetic.

* * * * *